US010671830B2

(12) United States Patent
Zeng et al.

(10) Patent No.: US 10,671,830 B2
(45) Date of Patent: Jun. 2, 2020

(54) ARRAY SUBSTRATE, DISPLAY PANEL AND DISPLAY DEVICE

(71) Applicant: Shanghai Tianma Micro-Electronics Co., Ltd., Shanghai (CN)

(72) Inventors: Yang Zeng, Shanghai (CN); Qing Zhang, Shanghai (CN); Lihua Wang, Shanghai (CN); Liang Xie, Shanghai (CN); Lingxiao Du, Shanghai (CN); Hong Ding, Shanghai (CN); Huiping Chai, Shanghai (CN); Kang Yang, Shanghai (CN); Qijun Yao, Shanghai (CN)

(73) Assignee: SHANGHAI TIANMA MICRO-ELECTRONICS CO., LTD., Shanghai (CN)

( * ) Notice: Subject to any disclaimer, the term of this patent is extended or adjusted under 35 U.S.C. 154(b) by 381 days.

(21) Appl. No.: 15/812,235

(22) Filed: Nov. 14, 2017

(65) Prior Publication Data

US 2018/0068166 A1 Mar. 8, 2018

(30) Foreign Application Priority Data

Jun. 19, 2017 (CN) .......................... 2017 1 0464898

(51) Int. Cl.
*G06K 9/00* (2006.01)
*G02F 1/1333* (2006.01)
(Continued)

(52) U.S. Cl.
CPC ........ *G06K 9/00067* (2013.01); *A61B 5/1172* (2013.01); *A61B 5/6898* (2013.01);
(Continued)

(58) Field of Classification Search
CPC ...... A61B 2562/0233; A61B 2562/046; A61B 5/1172; A61B 5/6898; G02F 1/13318;
(Continued)

(56) References Cited

U.S. PATENT DOCUMENTS

2006/0011913 A1* 1/2006 Yamazaki ............. G06F 3/0412
257/59
2015/0331508 A1* 11/2015 Nho ....................... G06F 3/0421
345/173

FOREIGN PATENT DOCUMENTS

CN 106295611 A 1/2017

* cited by examiner

*Primary Examiner* — Kim Y Vu
*Assistant Examiner* — Michael J Vanchy, Jr.
(74) *Attorney, Agent, or Firm* — Alston & Bird LLP

(57) ABSTRACT

An array substrate, a display panel and a display device are provided. The array substrate includes a substrate; a plurality of light-emitting units, which are in the display area of the substrate and include emission colors: a first color, a second color and a third color, where a light transmittance of the first color and a light transmittance of the second color are both greater than a light transmittance of the third color; and a plurality of first fingerprint recognition units and a plurality of second fingerprint recognition units, which are in the display area of the substrate. Each light-emitting unit serves as a light source of each fingerprint recognition unit, and each first fingerprint recognition unit and each second fingerprint recognition unit have different configuration parameters so as to detect a same electric signal value with respect to a reflector.

13 Claims, 29 Drawing Sheets

(51) Int. Cl.
  *G06K 9/20* (2006.01)
  *A61B 5/00* (2006.01)
  *A61B 5/1172* (2016.01)
  *G02F 1/133* (2006.01)
(52) U.S. Cl.
  CPC ....... *G02F 1/1333* (2013.01); *G06K 9/00033* (2013.01); *G06K 9/00046* (2013.01); *G06K 9/2018* (2013.01); *A61B 2562/0233* (2013.01); *A61B 2562/046* (2013.01); *G02F 1/13318* (2013.01); *G02F 1/13338* (2013.01)
(58) Field of Classification Search
  CPC ........... G06K 9/00033; G06K 9/00046; G06K 9/00067; G06K 9/2018
  See application file for complete search history.

ARRAY SUBSTRATE, DISPLAY PANEL AND DISPLAY DEVICE

CROSS-REFERENCES TO RELATED APPLICATIONS

This application claims priority to Chinese patent application No. CN201710464898.1, filed on Jun. 19, 2017, the disclosure of which is incorporated herein by reference in its entirety.

TECHNICAL FIELD

Embodiments of the present disclosure relate to fingerprint recognition techniques and, in particular, to an array substrate, a display panel and a display device.

BACKGROUND

A fingerprint is inherent for everybody and is unique. With the development of science and technology, various display devices having fingerprint recognition functions have appeared on the market. Such devices include mobile phones, tablet PCs, intelligent wearable equipment, etc. In this way, a user can undergo rights verification by simply touching, with a finger, a fingerprint recognition unit of a display device having a fingerprint recognition function before operating this device, thereby simplifying the rights verification process.

The fingerprint recognition unit is often provided in a non-display area of a display panel. When rights verification is performed for the display panel with such structure, the user needs to touch the fingerprint recognition unit intentionally. Undoubtedly, this will affect the user experience. Additionally, disposing the fingerprint recognition unit in the non-display area of the display panel reduces the screen-to-body ratio and goes against the trend towards a narrow bezel of the display panel.

SUMMARY

The present disclosure provides an array substrate, a display panel and a display device for improving the screen-to-body ratio and the fingerprint recognition accuracy of the display panel.

In a first aspect, an embodiment of the present disclosure provides an array substrate including a substrate, which includes a substrate comprising a display area with a non-display area surrounding the display area; a plurality of light-emitting units located in the display area of the substrate; a plurality of first fingerprint recognition units and a plurality of second fingerprint recognition units.

The plurality of light-emitting units includes a plurality of first light-emitting units configured to emit first color light, a plurality of second light-emitting units configured to emit second color light, and a plurality of third light-emitting units configured to emit third color light, and wherein a light transmittance of the first color light and that of the second color light are both greater than that of the third color light.

The plurality of first fingerprint recognition units and the plurality of second fingerprint recognition units are located in the display area of the substrate. A projection of each of the plurality of first fingerprint recognition units onto the substrate overlaps, at least in part, with a projection of an area between a respective one of the plurality of third light-emitting units one of a respective one of the plurality of first light-emitting units and a respective one of the plurality of second light-emitting units onto the substrate. A projection of each of the plurality of second fingerprint recognition units onto the substrate does not overlap with the projection of the area between the third light-emitting unit and one of the first light-emitting unit and the second light-emitting unit onto the substrate, and the projection of each of the plurality of second fingerprint recognition units onto the substrate overlaps at least in part with a projection of an area between the respective one of the plurality of first light-emitting units and the respective one of the plurality of second light-emitting units onto the substrate.

The plurality of light-emitting units are configured to: in a fingerprint recognition stage, serve as light sources for the plurality of first fingerprint recognition units and the plurality of second fingerprint recognition units, and the plurality of first fingerprint recognition units and the plurality of second fingerprint recognition units have different configuration parameters for detecting an electric signal value with respect to a reflector.

In a second aspect, an embodiment of the present disclosure provides a display panel including the array substrate of any embodiment of the present disclosure.

In a third aspect, an embodiment of the present disclosure provides a display device including the display panel of any embodiment of the present disclosure.

In embodiments of the present disclosure, the first fingerprint recognition units and the second fingerprint recognition units are disposed in the display area of the substrate. This solves the problem of a low screen-to-body ratio of an existing display panel, achieves the purpose of improving the low screen-to-body ratio of the display panel and meets the trend towards a narrow bezel of the display panel. Moreover, in embodiments of the present disclosure, each first fingerprint recognition unit and each second fingerprint recognition unit have different configuration parameters so as to detect the same electric signal value with respect to the same reflector. This improves the fingerprint recognition accuracy.

DETAILED DESCRIPTION

The present disclosure will be further described in detail with reference to the accompanying drawings and embodiments. It is to be understood that the embodiments set forth below are intended to explain and not to limit the present disclosure. For ease of description, only a part related to the present disclosure, rather than the whole structure, is illustrated in the accompanying drawings.

Skin prints (including fingerprint) of each person are different in terms of patterns, breakpoints and cross points, and are unique and constant for a life. Accordingly, a person can be associated with his fingerprint, and his true identity can be verified by comparing his fingerprint with pre-stored fingerprint data. This is the fingerprint recognition technology. Thanks to manufacturing techniques of integrated circuits and fast and reliable algorithm, the optical fingerprint recognition technology, which is a kind of the fingerprint recognition technology, has begun to appear in our daily life and has become the most in-depth, the most widely used, and the most mature technology in current biological assays. The optical fingerprint recognition technology works under such principles: Lights emitted from a light source in a display panel irradiate a touch body (e.g., a finger) and are reflected by the finger to form reflected lights, the reflected lights (i.e., fingerprint signal light) are transmitted to a fingerprint recognition unit, and then the photo signals transmitted to the fingerprint recognition unit are collected by the fingerprint recognition unit. A fingerprint has specific textures, so the reflected lights formed by various positions of the finger have different intensities, photo signals collected by different fingerprint recognition units are different, and accordingly, the true identity of the user is determined.

Figure 1:
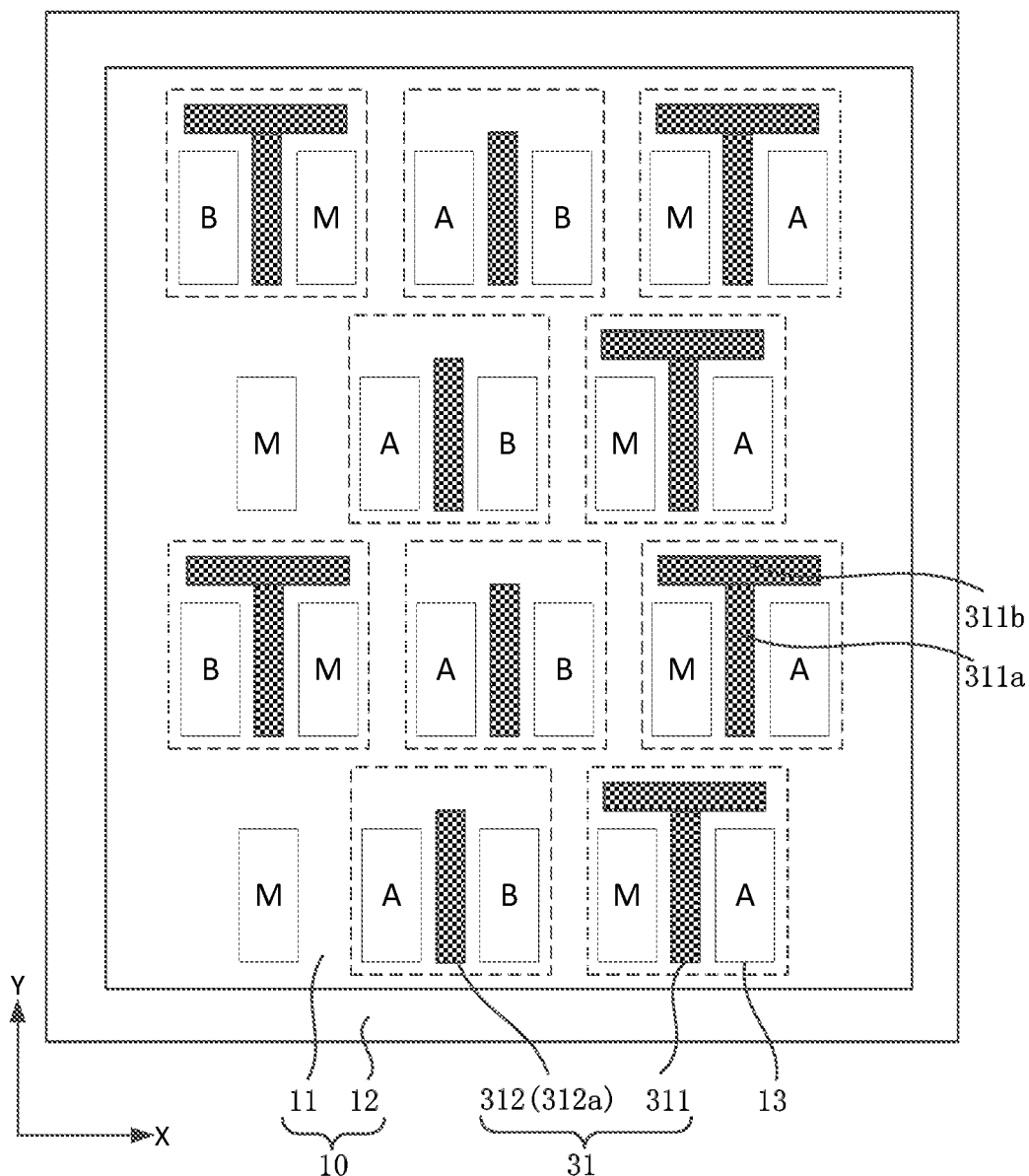
FIG. 1 is a schematic structural diagram of an array substrate according to an embodiment of the present disclosure.

FIG. 1 is a structural diagram of an array substrate according to an embodiment of the present disclosure. Referring to FIG. 1, the array substrate includes a substrate 10, which includes a display area 11 and a non-display area 12 around the display area 11; a plurality of light-emitting units 13, which are in the display area 11 of the substrate 10 and emission colors of which include: a first color A, a second color B and a third color M, where a light transmittance of the first color A and a light transmittance of the second color B are both greater than a light transmittance of the third color M; and a plurality of first fingerprint recognition units 311 and a plurality of second fingerprint recognition units 312, which are in the display area 11 of the substrate 10. A projection of each first fingerprint recognition unit 311 onto the substrate 10 coincides at least in part with a projection of an area between the light-emitting unit 13 with the third color M as the emission color and the light-emitting unit 13 with the first color A or the second color B as the emission color onto the substrate 10. (FIG. 1 illustrates an example in which the projection of each first fingerprint recognition unit 311 onto the substrate 10 is within the projection of the area between the light-emitting unit 13 with the third color M as the emission color and the light-emitting unit 13 with the first color A or the second color B as the emission color onto the substrate 10). A projection of each second fingerprint recognition unit 312 onto the substrate 10 does not coincide with the projection of the area between the light-emitting unit 13 with the third color M as the emission color and the light-emitting unit 13 with the first color A or the second color B as the emission color onto the substrate 10. The projection of each second fingerprint recognition unit 312 onto the substrate 10 coincides at least in part with a projection of an area between the light-emitting unit 13 with the first color A as the emission color and the light-emitting unit 13 with the second color B as the emission color onto the substrate 10. FIG. 1 illustrates an example in which the second fingerprint recognition unit 312 is within the projection of the area between the light-emitting unit 13 with the first color A as the emission color and the light-emitting unit 13 with the second color B as the emission color onto the substrate 10. In a fingerprint recognition stage, the light-emitting unit 13 serves as light sources of the fingerprint recognition units 31 (including first fingerprint recognition unit 311 and the second fingerprint recognition unit 312), and the first fingerprint recognition unit 311 and the second fingerprint recognition unit 312 have different configuration parameters such that for a same reflector, an electric signal value detected by the first fingerprint recognition unit 311 and an electric signal value detected by the second fingerprint recognition unit 312 are the same.

In embodiments of the present disclosure, the first fingerprint recognition units 311 and the second fingerprint recognition units 312 are disposed in the display area 11 of the substrate 10. This solves the problem of a low screen-to-body ratio of an existing display panel, achieves the purpose of improving a low screen-to-body ratio of a display panel and meets the trend towards a narrow bezel of the display panel.

In the present embodiment, the configuration parameters indicate values representing performance characteristics of all components in the fingerprint recognition unit 31. The fingerprint recognition accuracy of each fingerprint recognition unit 31 is evaluated according to the configuration parameters. The configuration parameters include an area of a photosurface area of the fingerprint recognition unit 31, brightness of light-emitting units 13 around the fingerprint recognition unit 31, a capacitance value of a storage capacitor in the fingerprint recognition unit 31, and a light sensitivity of a photosensitive diode in the fingerprint recognition unit 31.

A light transmittance of a display panel is the efficiency of the display panel being passed through by the light and is a ratio of luminous flux through the display panel to the incident luminous flux on the display panel. Studies show that various films (including an organic insulation layer, an inorganic insulation layer and a polarizer, etc.) in the display panel have different absorption capacities for lights in different colors, making light in different colors has different light transmissivities. Typically, if the emission colors of the light-emitting units in the display panel include red, green and blue, then the light transmittance of the red light and the light transmittance of the green light are both greater than the light transmittance of the blue light. Here the first color A is red, the second color B is green and the third color M is blue.

In practice, in a fingerprint recognition process, the light-emitting units 13 around a first fingerprint recognition unit 311 serve as the light sources of the first fingerprint recognition unit 311. That is, lights emitted from the light-emitting units 13 around the first fingerprint recognition unit 311 are reflected by a touch body and then transmitted into the first fingerprint recognition unit 311 so that fingerprint recognition is performed. The projection of the first fingerprint recognition unit 311 onto the substrate 10 coincides at least in part with the projection of the area between the light-emitting unit 13 with the third color M as the emission color and the light-emitting unit 13 with the first color A (or the second color B) as the emission color onto the substrate 10, so that each first fingerprint recognition unit 311 receives photo signals from the light-emitting unit 13 with the third color M as the emission color and the light-emitting unit 13 with the first color A (or the second color B) as the emission color.

Similarly, in practice, in the fingerprint recognition process, the light-emitting units 13 around a second fingerprint recognition unit 312 serve as the light sources of the second fingerprint recognition unit 312. That is, lights emitted from the light-emitting units 13 around the second fingerprint recognition unit 312 are reflected by the touch body and then transmitted into the second fingerprint recognition unit 312 so that fingerprint recognition is performed. The projection of the second fingerprint recognition unit 312 onto the substrate 10 coincides at least in part with the projection of the area between the light-emitting unit 13 with the first color A as the emission color and the light-emitting unit 13 with the second color B as the emission color onto the substrate 10, so that each second fingerprint recognition unit 312 receives photo signals from the light-emitting unit 13 with the first color A as the emission color and the light-emitting unit 13 with the second color B as the emission color.

Since the light transmittance of the first color A and the light transmittance of the second color B are both greater than the light transmittance of the third color M, if provided with the same configuration parameters, the first fingerprint recognition unit 311 and the second fingerprint recognition unit 312 receive different luminous fluxes with respect to the same reflector (e.g., a flat mirror) and detect different fingerprint signals with respect to the same touch body. This causes a large fingerprint recognition error and a low fingerprint recognition accuracy during fingerprint recognition.

In the above solutions, the first fingerprint recognition unit 311 and the second fingerprint recognition unit 312 have different configuration parameters such that the first fingerprint recognition unit 311 and the second fingerprint recognition unit 312 can detect the same electric signal value with respect to the same reflector. This achieves the purpose of reducing the fingerprint recognition error and improving the fingerprint recognition accuracy during fingerprint recognition.

The first fingerprint recognition unit 311 and the second fingerprint recognition unit 312 can be configured to have different configuration parameters using various methods that are described below in detail by way of typical examples. The examples described herein are intended to illustrate and not to limit the present disclosure.

Referring to FIG. 1, each fingerprint recognition unit 31 includes a photosurface located on a surface of the fingerprint recognition unit 31 facing a display side. The area of the photosurface of the fingerprint recognition unit 31 is one of the configuration parameters. Optionally, the area of the photosurface of the first fingerprint recognition unit 311 is greater than the area of the photosurface of the second fingerprint recognition unit 312. Here the photosurface is configured to receive reflected lights reflected by a touch body.

Specifically, as shown in FIG. 1, the light transmittance of the first color A and the light transmittance of the second color B are both greater than the light transmittance of the third color M, but the area of the photosurface of each first fingerprint recognition unit 311 is set to greater than the area of the photosurface of each second fingerprint recognition unit 312 such that each first fingerprint recognition unit 311 and each second fingerprint recognition unit 312 receive the same luminous flux with respect to the same reflector (e.g., a flat mirror). Based on the same luminous flux, the first fingerprint recognition unit 311 and the second fingerprint recognition unit 312 detect the same fingerprint signal, thereby reducing the fingerprint recognition error and improving the fingerprint recognition accuracy.

The area of the photosurface of the first fingerprint recognition unit 311 may be set to greater than the area of the photosurface of the second fingerprint recognition unit 312 based on an arrangement of the light-emitting units 13.

For example, as illustrated in FIG. 1, the light-emitting units 13 are arranged in an array. The light-emitting units 13 in each odd-numbered row are arranged in the order of one light-emitting unit 13 in the second color B, one light-emitting unit 13 in the third color M, one light-emitting unit 13 in the first color A, one light-emitting unit 13 in the second color B, . . . . The light-emitting units 13 in each even-numbered row are arranged in the order of one light-emitting unit 13 in the third color M, one light-emitting unit 13 in the first color A, one light-emitting unit 13 in the second color B, one light-emitting unit 13 in the third color M, . . . . Any light-emitting unit 13 in each even-numbered row and two adjacent light-emitting units 13 adjacent thereto in a same odd-numbered row are arranged triangularly.

According to the arrangement of the light-emitting units 13 in FIG. 1, the photosurface of each first fingerprint recognition unit 311 includes a first portion 311a and a second portion 311b. A projection of the first portion 311a onto the substrate 10 is within the projection of the area between the light-emitting unit 13 with the third color M as the emission color and the light-emitting unit 13 with the first color A (or the second color B) as the emission color onto the substrate 10, where the light-emitting unit 13 with the third color M as the emission color and the light-emitting unit 13 with the first color A (or the second color B) as the emission color are adjacent to each other in a row direction (X-axis direction in FIG. 1). A projection of the second portion 311b onto the substrate 10 is within a projection of an area between respective two rows of the light-emitting units 13 onto the substrate 10. Exemplarily, referring to FIG. 1, the first portion 311a is shaped as a strip extending in a column direction (Y-axis direction in FIG. 1), the second portion 311b is shaped as a strip extending in the row direction (X-axis direction in FIG. 1), and the first portion 311a and the second portion 311b form a T-shaped structure.

The photosurface of each second fingerprint recognition unit 312 includes a third portion 312a. A projection of the third portion 312a onto the substrate 10 is within the projection of the area between the light-emitting unit 13 with the first color A as the emission color and the light-emitting unit with the second color B as the emission color onto the substrate 10, where the light-emitting unit 13 with the first color A as the emission color and the light-emitting unit with the second color B as the emission color are adjacent to each other in the row direction. The third portion 312a is shaped as a strip extending in the column direction (Y-axis direction in FIG. 1).

The above solutions enable the first fingerprint recognition unit 311 and the second fingerprint recognition unit 312 to receive the same luminous flux, thereby reducing the fingerprint recognition error and improving the fingerprint recognition accuracy.

It should be noted that FIG. 1 just provides one arrangement of the light-emitting units 13. This arrangement is just an example of the present disclosure and is not intended to limit the present disclosure. In practice, the light-emitting units 13 in the display panel may have various arrangements, and the photosurfaces of the fingerprint recognition units 31 may be configured in various ways based on the various arrangements of the light-emitting units 13.

Figure 2:
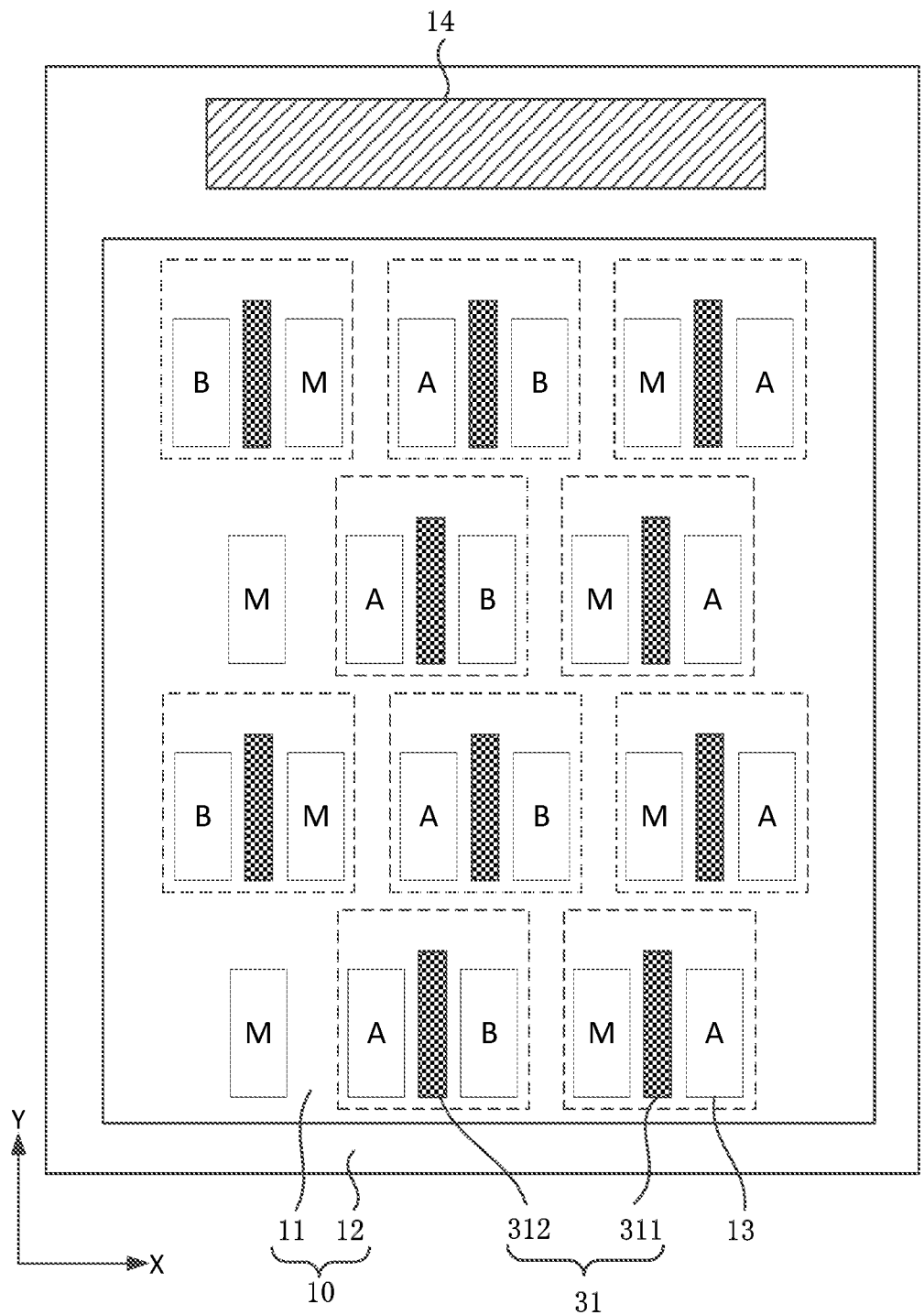
FIG. 2 is a schematic structural diagram of another array substrate according to an embodiment of the present disclosure.

The fingerprint recognition unit 31 performs fingerprint recognition relying on lights emitted from the light-emitting unit 13, so the light-emitting unit 13 can be regarded as a part of the fingerprint recognition unit 31. In this case, the brightness of the light-emitting unit 13 is one of configuration parameters of the fingerprint recognition unit 31. FIG. 2 is a structural diagram of another array substrate according to an embodiment of the present disclosure. Optionally, the brightness of the light-emitting unit 13 with the third color M as the emission color and the light-emitting unit 13 with the first color A (or the second color B) as the emission color around the first fingerprint recognition unit 311 is configured to be greater than the brightness of the corresponding light-emitting unit 13 with the first color A as the emission color and the corresponding light-emitting unit 13 with the second color B as the emission color around the second fingerprint recognition unit 312. Such configuration increases luminous flux received by the first fingerprint recognition unit 311 and reduces luminous flux received by the second fingerprint recognition unit 312, so that the first fingerprint recognition unit 311 and the second fingerprint recognition unit 312 receive the same luminous flux. Based on the same luminous flux, the fingerprint signal detected by the first fingerprint recognition unit 311 and the fingerprint signal detected by the second fingerprint recognition unit 312 are the same, thereby reducing the fingerprint recognition error and improving the fingerprint recognition accuracy.

Optionally, as illustrated in FIG. 2, the array substrate includes a driver chip 14. In the fingerprint recognition stage, the driver chip 14 enables the brightness of the light-emitting unit 13 with the third color M as the emission color and the light-emitting unit 13 with the first color A (or the second color B) as the emission color around the first fingerprint recognition unit 311 to be greater than the brightness of the corresponding light-emitting unit 13 with the first color A as the emission color and the corresponding light-emitting unit 13 with the second color B as the emission color around the second fingerprint recognition unit 312. This enables the first fingerprint recognition unit 311 and the second fingerprint recognition unit 312 to receive the same luminous flux, thereby reducing the fingerprint recognition error and improving the fingerprint recognition accuracy. Optionally, the driver chip 14 may control the brightness of the light-emitting units 13 by inputting voltage signals or current signals in different magnitudes to the light-emitting units 13 around the first fingerprint recognition unit 311 and the light-emitting units 13 around the second fingerprint recognition unit 312. Optionally, when stronger voltage signals or current signals are inputted, the light-emitting units 13 have a higher brightness. Exemplarily, the brightness of each light-emitting unit 13 is divided into 256 scales. The light-emitting unit 13 is turned off and does not emit light at a brightness scale of 0 and is the brightest at a brightness scale of 255. Optionally, referring to FIG. 2, the brightness of the light-emitting units 13 around the first fingerprint recognition unit 311 is set to 255 and the brightness of the light-emitting units 13 around the second fingerprint recognition unit 312 is set to 150, so that the first fingerprint recognition unit 311 and the second fingerprint recognition unit 312 receive the same luminous flux.

Figure 3:
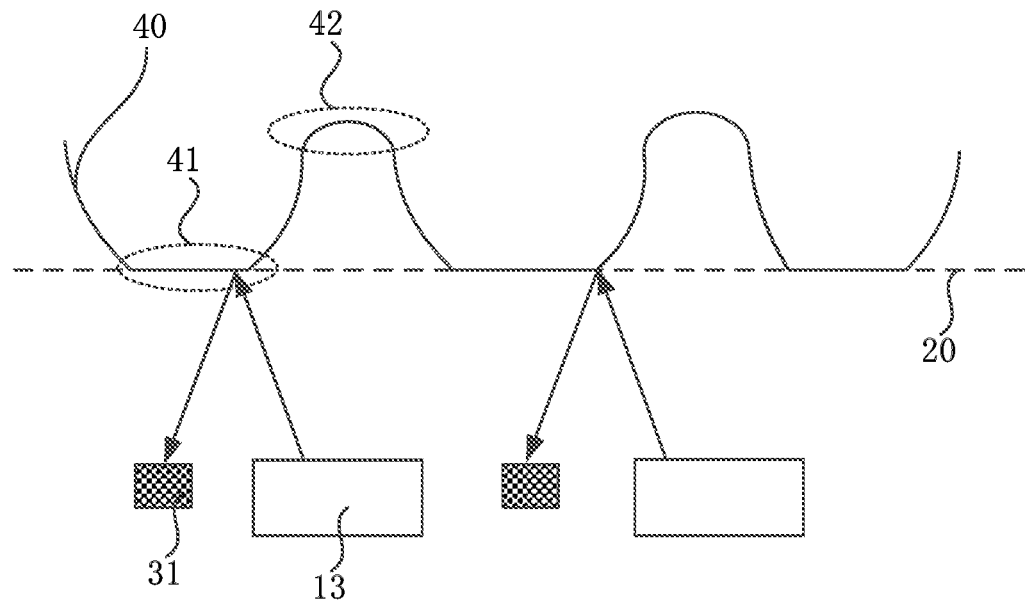
FIG. 3 is a schematic diagram illustrating a working principle of a fingerprint recognition unit according to an embodiment of the present disclosure.

FIG. 3 is a schematic diagram illustrating a working principle of the fingerprint recognition unit according to an embodiment of the present disclosure. Optionally, as illustrated in FIG. 3, lights emitted from light-emitting units 13 are reflected by a touch body 40 and then transmitted into the fingerprint recognition units 31 (including the first fingerprint recognition units 311 and the second fingerprint recognition units 312) so that fingerprint recognition is performed.

Figure 4A:
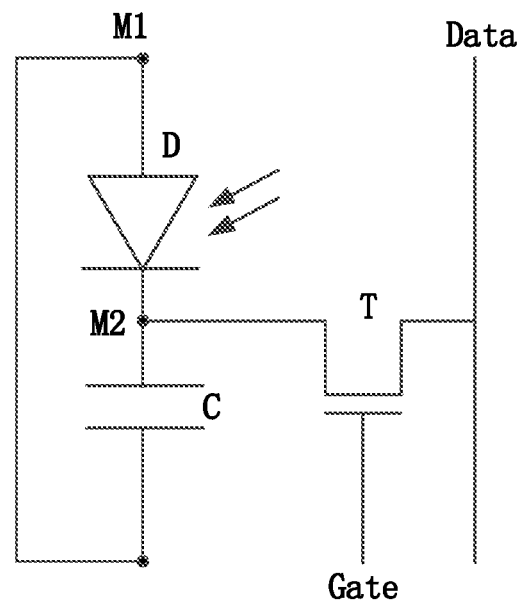
FIG. 4A is a schematic circuit diagram of a fingerprint recognition unit according to an embodiment of the present disclosure.
Figure 4B:
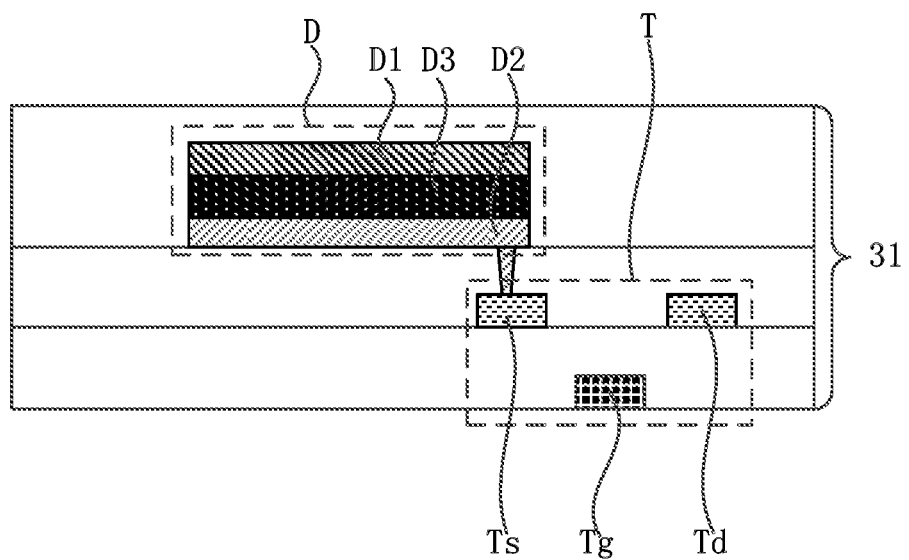
FIG. 4B is a schematic cross sectional diagram illustrating film stack of a fingerprint recognition unit according to an embodiment of the present disclosure.

FIG. 4A is a circuit diagram of a fingerprint recognition unit according to an embodiment of the present disclosure. FIG. 4B is a structural diagram illustrating films of a fingerprint recognition unit according to an embodiment of the present disclosure. Referring to FIGS. 4A and 4B, the fingerprint recognition unit 31 may include a photosensitive diode D, a storage capacitor C and a thin film transistor T. An anode D1 of the photosensitive diode D is electrically connected to a first electrode of the storage capacitor C, and a cathode D2 of the photosensitive diode D is electrically connected to a second electrode of the storage capacitor C and to a source electrode Ts of the thin film transistor T. A gate electrode Tg of the thin film transistor T is electrically connected to a switch control line Gate, and a drain electrode Td of the thin film transistor T is electrically connected to a signal line Data. The photosensitive diode D is configured to convert light reflected by a touch body into a current signal.

Specifically, the photosensitive diode D further includes a PIN junction D3 between the anode D1 and the cathode D2. The cathode D2 is formed from light-proof metal, and a border of the PIN junction D3 does not exceed a border of the cathode D2. The anode D1 of the photosensitive diode D is on a side of the PIN junction D3 facing away from the cathode D2. The PIN junction D3 is photosensitive and unilaterally conductive. When no light is available, the PIN junction D3 has a small reverse saturation leakage current, i.e., dark current. In this case, the photosensitive diode D is turned off. When exposed to light, the reverse saturation leakage current of the PIN junction D3 dramatically increases to form a light current. The light current varies with an intensity of incident light.

Exemplarily, a fingerprint recognition principle will be described below in detail with reference to FIGS. 3, 4A and 4B. In the fingerprint recognition stage, a low-voltage signal (e.g., a constant voltage signal of −5 V) is inputted to a node M1 and a high-voltage signal (e.g., a constant voltage signal of 1.5 V) is inputted to the signal line data. The fingerprint recognition stage includes a preparation stage, a fingerprint signal acquisition stage and a fingerprint signal detection stage. In the preparation stage, the driver chip (not illustrated in FIGS. 3, 4A and 4B) electrically connected to the fingerprint recognition unit 13 enables the thin film transistor T of the fingerprint recognition unit 13 to be turned on via the switch control line Gate. Then the storage capacitor C is charged until the charging is completed. In the fingerprint signal acquisition stage, the thin film transistor T of the fingerprint recognition unit 13 is turned off via the switch control line Gate. When a user presses a finger against a touchable surface 20 of a display panel, lights emitted from the light-emitting units 13 are transmitted to the finger and then are reflected by a surface of the fingerprint to form reflected lights. The reflected lights formed by fingerprint reflection are transmitted into the fingerprint recognition unit 13, received by the photosensitive diode D of the fingerprint recognition unit 13, and then converted into a light current. The light current is transmitted in a direction from a node M2 to a node M1 so that an electric potential of M2 is changed and the storage capacitor C is discharged. In the fingerprint signal detection stage, various methods may be used to detect a fingerprint signal. For example, magnitude of the light current may be determined by directly measuring a variation in the electric potential of the node M2. Alternatively, magnitude of the light current may be determined when the thin film transistor T of the fingerprint recognition unit 13 is turned on via the switch control line Gate (in which case a potential difference exists between the two electrodes of the storage capacitor C when the storage capacitor C is charged) and then the quantity of electric charge of the storage capacitor C is detected.

Referring to FIG. 3, a ridge 41 of the fingerprint pressed against the display panel is in contact with the surface of the display panel while a valley 42 is not, thus causing a difference between light refractive index on the valley 42 and light refractive index on the ridge 41 and further causing a difference between an intensity of reflected light formed at the ridge 41 received by the fingerprint recognition unit 13 and an intensity of reflected light formed at the valley 42 received by the fingerprint recognition unit 13. As a result, the magnitude of the light current converted from the reflected light formed at the ridge 41 is different from the magnitude of the light current converted from the reflected light formed at the valley 42. Fingerprint recognition is performed according to the magnitude of the light current.

For the case where the magnitude of the light current is determined by directly detecting the variation in the electric potential of the node M2 in the fingerprint signal detection stage, optionally, the capacitance value of the storage capacitor of the first fingerprint recognition unit 311 is set to less than that of the second fingerprint recognition unit 312. Here the capacitance value of the storage capacitor is one of the configuration parameters of the fingerprint recognition unit 31. Referring to FIG. 4A, the variation in the electric potential of the node M2 is calculated based on a formula $$\Delta U = \frac{\Delta Q}{C} = \frac{It}{C}.$$

In the formula, C denotes the capacitance value of the storage capacitor of the first fingerprint recognition unit, ΔQ denotes a change in the amount of the charge of the storage capacitor of the fingerprint recognition unit in the fingerprint recognition stage, I denotes the light current of the fingerprint recognition unit, and t denotes the duration of the light current. In the fingerprint signal acquisition stage, a light transmittance of the first color A and a light transmittance of the second color B are both greater than a light transmittance of the third color M, so that the first fingerprint recognition unit 311 receives a lower luminous flux than the second fingerprint recognition unit 312 with respect to a same reflector (e.g., a flat mirror) and the light current formed in the first fingerprint recognition unit 311 is less than the light current formed in the second fingerprint recognition unit 312. On this basis, the capacitance value of the storage capacitor of the first fingerprint recognition unit 311 is set to less than that of the second fingerprint recognition unit 312, so that the variation in the electric potential of the node M2 of the first fingerprint recognition unit 311 is the same as the variation in the electric potential of the node M2 of the second fingerprint recognition unit 312, i.e., the fingerprint signal detected by the first fingerprint recognition unit 311 and the fingerprint signal detected by the second fingerprint recognition unit 312 are equal, thereby reducing the fingerprint recognition error and improving the fingerprint recognition accuracy.

Optionally, referring to FIG. 4A, the storage capacitor includes the first electrode and the second electrode. If the storage capacitor is a plate capacitor, the capacitance value C of the storage capacitor is calculated using a formula $$C = \frac{\varepsilon S}{4\pi kq}.$$

In the formula, $\varepsilon$ denotes an dielectric constant and is determined by a medium between the first electrode and the second electrode, S denotes enfilade area of the first electrode and the second electrode of the storage capacitor, q denotes a distance between the first electrode and the second electrode of the storage capacitor, k denotes an electrostatic force constant, and $\pi$ denotes a ratio of the circumference of a circle to its diameter. According to the calculation formula of the capacitance value C, the distance q between the first electrode and the second electrode is inversely proportional to the capacitance value C and the opposing area S between the first electrode and the second electrode is directly proportional to the capacitance value C on the premise that the other parameters in the formula are constants.

On this basis, optionally, the distance q between the first electrode and the second electrode of the storage capacitor of the first fingerprint recognition unit 311 is set to greater than that of the second fingerprint recognition unit 312, and/or the enfilade area between the first electrode and the second electrode of the storage capacitor of the first fingerprint recognition unit 311 is set to less than that of the second fingerprint recognition unit 312, so that the capacitance value of the storage capacitor of the first fingerprint recognition unit 311 is less than that of the second fingerprint recognition unit 312, thereby achieving the purpose of reducing the fingerprint recognition error and improving the fingerprint recognition accuracy.

Figure 5A:
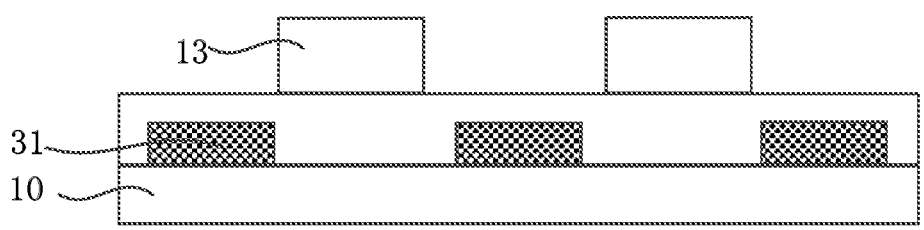
FIG. 5A is a schematic cross sectional diagram of another array substrate according to an embodiment of the present disclosure.
Figure 5B:
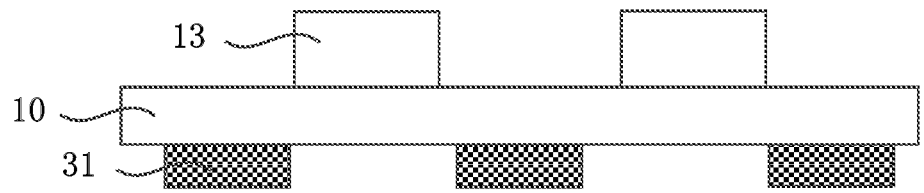
FIG. 5B is a schematic cross sectional diagram of another array substrate according to an embodiment of the present disclosure.
Figure 5C:
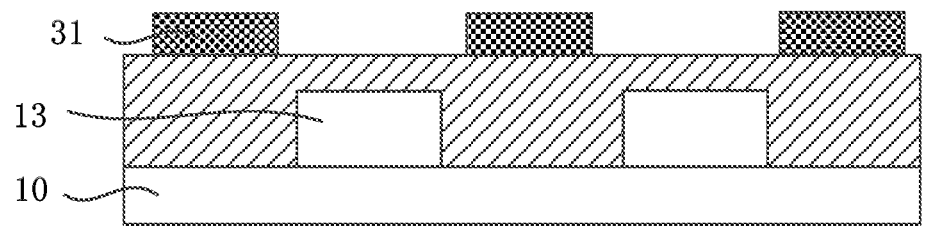
FIG. 5C is a schematic cross sectional diagram of another array substrate according to an embodiment of the present disclosure.
Figure 5D:
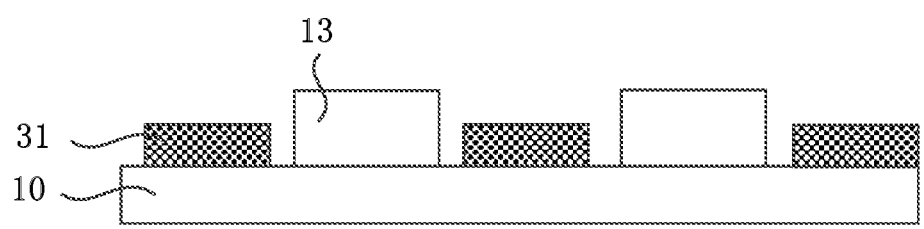
FIG. 5D is a schematic cross sectional diagram of another array substrate according to an embodiment of the present disclosure.

Optionally, as illustrated in FIG. 5A, the fingerprint recognition units 31 (including first light-emitting units 311 and second light-emitting units 312) are located between a substrate 10 and the light-emitting units 13; or as illustrated in FIG. 5B, the fingerprint recognition units 31 (including the first light-emitting units 311 and the second light-emitting units 312) are located on a side of the substrate 10 facing away from the light-emitting units 13; or as illustrated in FIG. 5C, the fingerprint recognition units 31 (including the first light-emitting units 311 and the second light-emitting units 312) are located on a side of the light-emitting units 13 facing away from the substrate 10; or as illustrated in FIG. 5D, the fingerprint recognition units 31 (including the first light-emitting units 311 and the second light-emitting units 312) are located in a same layer as the light-emitting units 13 and between respective two adjacent light-emitting units 13.

An embodiment of the present disclosure provides a display panel including the array substrate of any embodiment of the present disclosure. Optionally, the display panel may be a liquid crystal display panel or an organic light-emitting display panel.

Figure 6A:
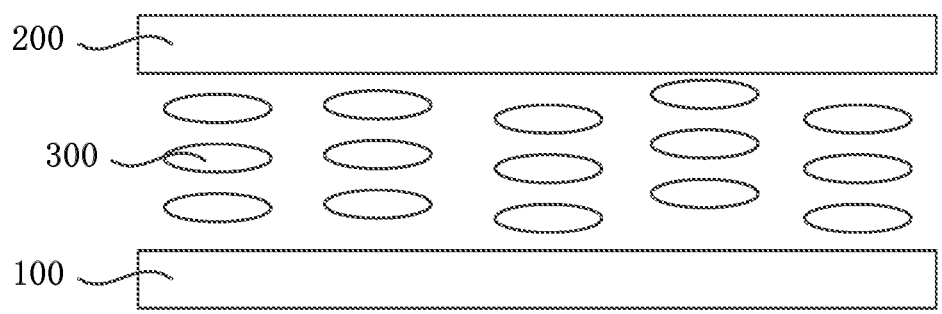
FIG. 6A is a conceptual diagram of a display panel according to an embodiment of the present disclosure.

FIG. 6A is a structural diagram of a display panel according to an embodiment of the present disclosure. Referring to FIG. 6A, the display panel is a liquid crystal display panel, and, in addition to the array substrate 100 of any embodiment of the present disclosure, the display panel further includes a color filter substrate 200 opposite to the array substrate 100, and a liquid crystal layer 300 between the array substrate 100 and the color filter substrate 200.

In the liquid crystal display panel, the array substrate 100 is provided with a plurality of scanning lines (not illustrated in FIG. 6A) extending in a first direction and arranged in a second direction and a plurality of data lines (not illustrated in FIG. 6A) extending in the second direction and arranged in the first direction. The first direction intersects the second direction. The scanning lines and the data lines intersect to define a plurality of pixel units. Here the pixel units are the light-emitting units 13 described herein.

Figure 6B:
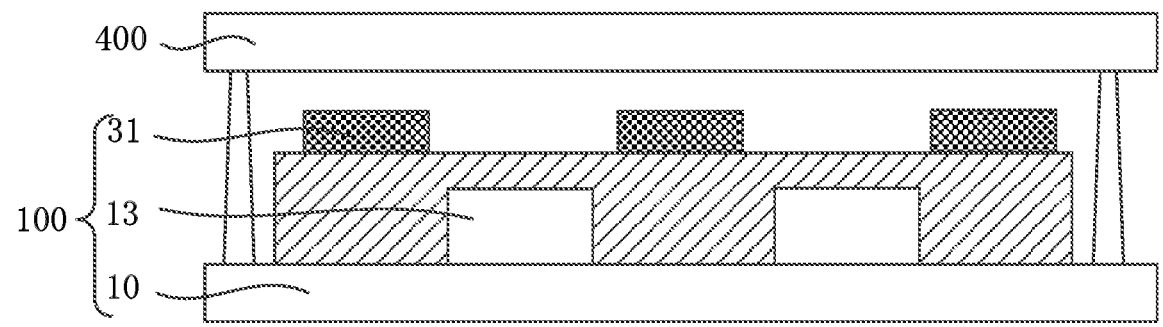
FIG. 6B is a schematic cross sectional diagram of another display panel according to an embodiment of the present disclosure.

FIG. 6B is a structural diagram of another display panel according to an embodiment of the present disclosure. Referring to FIG. 6B, the display panel is an organic light-emitting display panel, and, in addition to the array substrate 100 of any embodiment of the present disclosure, the display panel further includes a cover plate 400 opposite to the array substrate 100.

In the organic light-emitting display panel, a light-emitting unit may include an anode, a light-emitting layer and a cathode, etc. (not illustrated in FIG. 6A). The light-emitting layer is sandwiched between the anode and the cathode. Emission colors of the light-emitting layer may include red, green and blue.

For the above solutions where the fingerprint recognition units 31 (including the first light-emitting units 311 and the second light-emitting units 312) are located on the side of the substrate 10 facing away from the light-emitting units 13, or the fingerprint recognition units 31 (including the first light-emitting units 311 and the second light-emitting units 312) are located on the side of the light-emitting units 13 facing away the substrate 10, optionally, a first polarizer is disposed on a light-emitting surface of the light-emitting units 13 and a second polarizer is disposed between the fingerprint recognition units 31 and the light-emitting units 13. In this way, through cooperation between the first polarizer and the second polarizer, fingerprint signal light can pass through the first polarizer and the second polarizer without loss of light intensity and the second polarizer can at least reduce an intensity of the fingerprint noise light (the light not reflected by a touch body) before the fingerprint noise light reaches the fingerprint recognition layer. This reduces interference of the fingerprint noise light and improves a signal-to-noise ratio, thereby improving the fingerprint recognition accuracy of the fingerprint recognition units. Here the fingerprint noise light may include a part of the lights leaking from a light-emitting structure in a display module towards the light-emitting units.

Optionally, the second polarizer may be a linear polarizer or a circular polarizer that may reduce the intensity of the fingerprint noise light by half. When the second polarizer is a linear polarizer, to enable the fingerprint signal light to pass through the first polarizer and the second polarizer without loss of light intensity, the first polarizer is also a linear polarizer, and the first polarizer and the second polarizer are configured to have a same polarization direction. When the second polarizer is a circular polarizer, to enable the fingerprint signal light to pass through the first polarizer and the second polarizer without loss of light intensity, the first polarizer is a circular polarizer matching the second polarizer.

Figure 7:
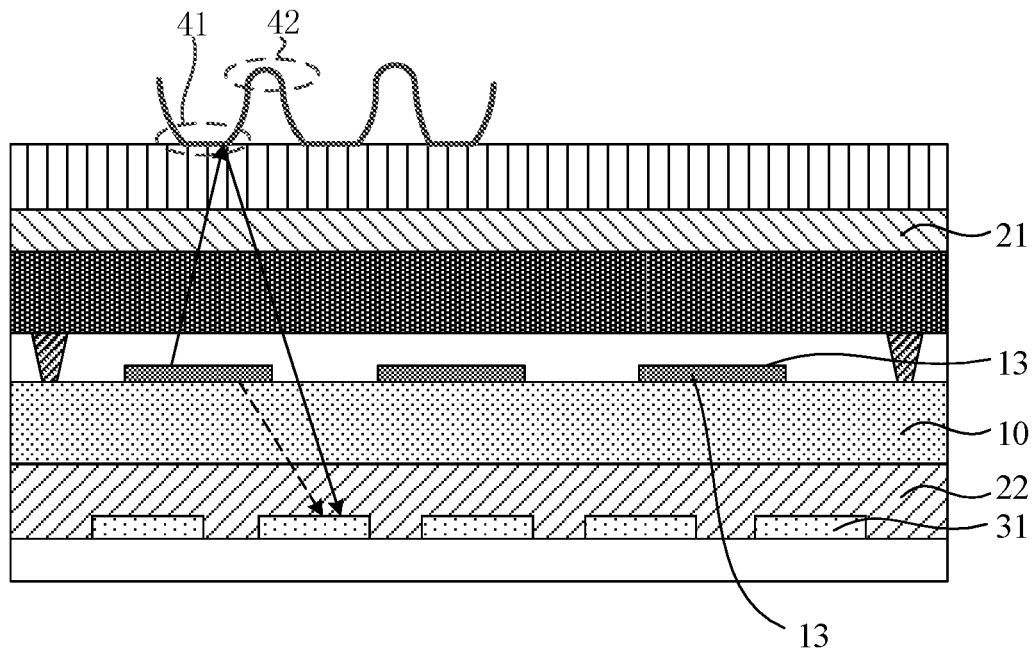
FIG. 7 is a schematic cross sectional diagram of another display panel according to an embodiment of the present disclosure.

Exemplarily, FIG. 7 is a structural diagram of a display panel according to an embodiment of the present disclosure. As illustrated in FIG. 7, fingerprint recognition units 31 are located on the side of the substrate 10 facing away from the light-emitting units 13, a first polarizer 21 is disposed on a light-emitting surface of the light-emitting units 13, and a second polarizer 22 is disposed between the fingerprint recognition units 31 and the light-emitting units 13.

Since the light-emitting units 13 serve as light sources for both image display and fingerprint recognition, the light-emitting units 13 emit light in both the display stage and the fingerprint recognition stage. In the display stage, light emission driving signals are inputted to the light-emitting units 13. In the fingerprint recognition stage, light emission driving signals are inputted to at least one of the light-emitting units 13. Therefore, based on the above solutions, the display panel of the present embodiment further includes a first display driver circuit (not illustrated in the figure) configured to output driving signals to drive at least one of the light-emitting units 13 for providing light sources for the fingerprint recognition units 31.

Optionally, in the present embodiment, the first polarizer may include a first linear polarizer, the second polarizer may include a second linear polarizer, and the first polarizer and the second polarizer may have a same polarization direction.

Referring to FIG. 7, solid arrows indicate lights emitted from the light-emitting unit 13 to a light-emitting surface and fingerprint signal lights after reflected by a touch body, and a dotted arrow indicates lights leaking from the light-emitting unit 13 towards the fingerprint recognition unit 31. The lights emitted from the light-emitting unit 13 are converted to linear polarized lights after passing through the first polarizer 21. After reflected by the touch body, the linear polarized lights remain linear polarized lights (now referred to as fingerprint signal lights) with an unchanged polarization direction and pass through the first polarizer 21 once again without loss of light intensity. Then the fingerprint signal lights pass through the second polarizer 22 and reach the fingerprint recognition unit 31 without loss of light intensity because the first polarizer 21 and the second polarizer 22 have the same polarization direction. In contrast, the lights leaking from the light-emitting units 13 are evenly distributed in various polarization directions, but have only one polarization direction after passing through the second polarizer 22 and lose half of light intensity. Therefore, the light intensity of the lights leaking from the light-emitting units 13 have been reduced dramatically when reaching the fingerprint recognition units 31. In summary, the intensity of fingerprint noise lights is weakened while the intensity of the fingerprint signal light is not changed, so that a signal-to-noise ratio of the fingerprint recognition unit 31 is improved and thus fingerprint recognition accuracy of the fingerprint recognition unit 31 is improved.

Additionally, in the embodiment of the present disclosure, the first polarizer may include laminated first quarter-wave plate and third linear polarizer, and the first quarter-wave plate is on a side of the third linear polarizer facing the light-emitting unit 13; and the second polarizer may include laminated second quarter-wave plate and fourth linear polarizer, and the second quarter-wave plate is on a side of the fourth linear polarizer facing an organic light-emitting layer.

The first quarter-wave plate and the second quarter-wave plate have the same material and thickness.

Facing a direction in which the fingerprint signal light is transmitted and using an anti-clockwise direction as a positive direction, an included angle between an optical axis direction of the first quarter-wave plate and a polarization direction of the third linear polarizer is 45°, and an included angle between an optical axis direction of the second quarter-wave plate and a polarization direction of the fourth linear polarizer is −45°. Alternatively, the included angle between the optical axis direction of the first quarter-wave plate and the polarization direction of the third linear polarizer is −45°, and the included angle between the optical axis direction of the second quarter-wave plate and the polarization direction of the fourth linear polarizer is 45°. Thus, both the first polarizer and the second polarizer are circular polarizers.

Figure 8A:
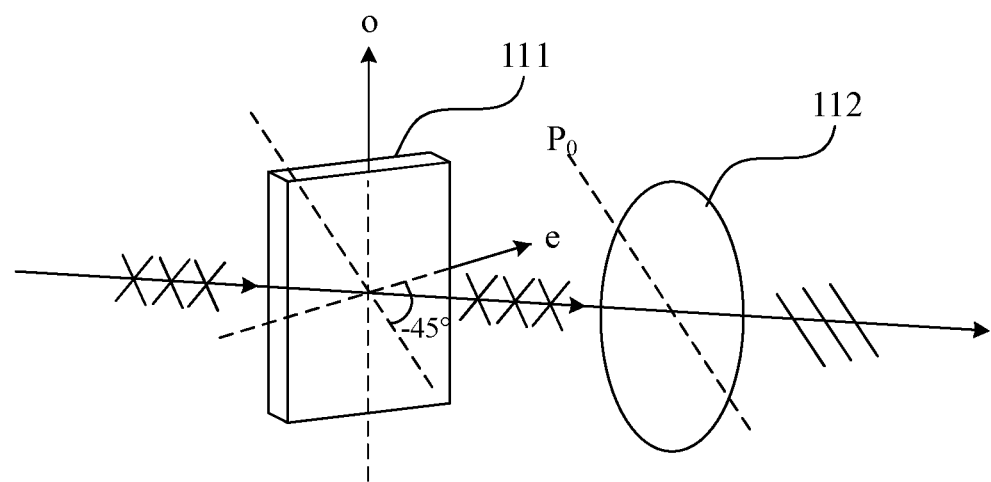
FIG. 8A is a schematic diagram illustrating a light path before light emitted from a light-emitting unit is reflected by a touch body according to an embodiment of the present disclosure.
Figure 8B:
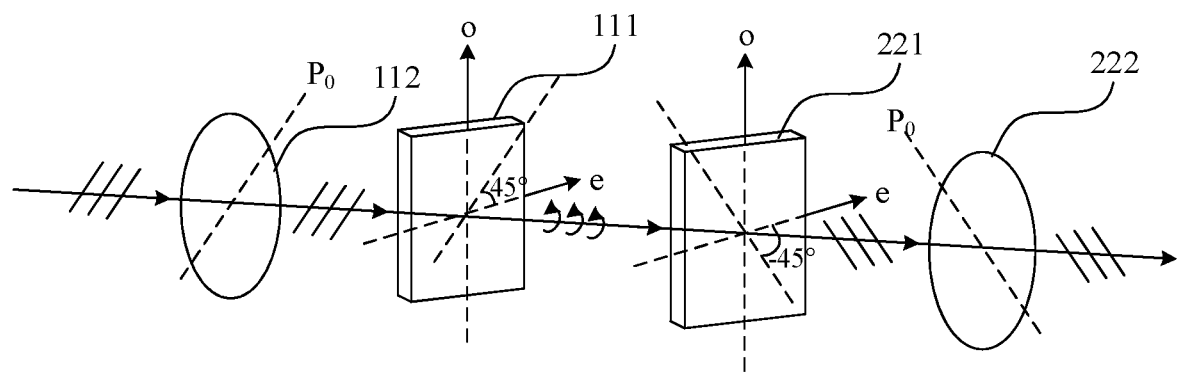
FIG. 8B is a schematic diagram illustrating a light path after light emitted from a light-emitting unit is reflected by a touch body according to another embodiment of the present disclosure.
Figure 9:
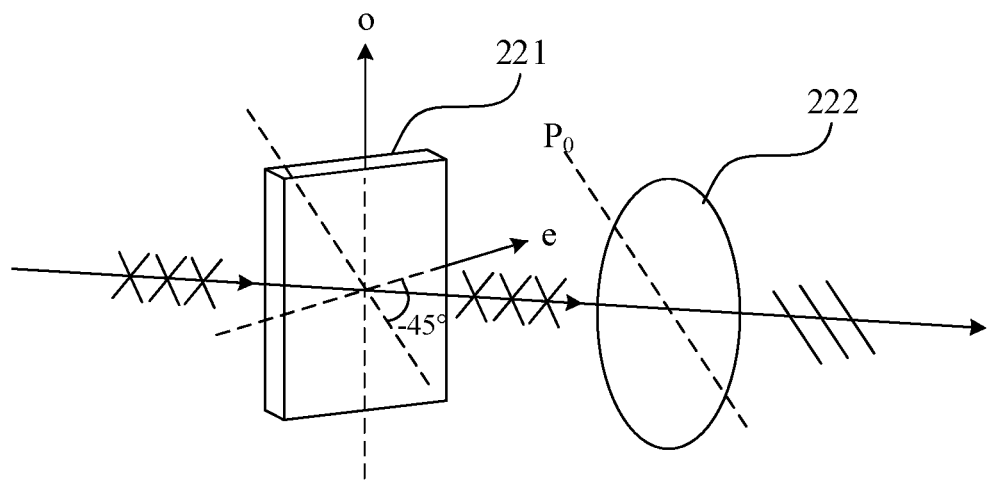
FIG. 9 is a schematic diagram illustrating a light path of noise in fingerprint signal according to an embodiment of the present disclosure.

Exemplarily, facing the direction in which the fingerprint signal light is transmitted and using the anti-clockwise direction as the positive direction, the included angle between the optical axis direction of the first quarter-wave plate and the polarization direction of the third linear polarizer is 45°, and the included angle between the optical axis direction of the second quarter-wave plate and the polarization direction of the fourth linear polarizer is −45°. In the example, the first quarter-wave plate and the second quarter-wave plate use calcite as their material and use an axes e thereof as their optical axes. Referring to FIG. 7, in the fingerprint recognition stage, as illustrated in FIG. 8A, facing the direction in which the light emitted from the light-emitting unit 13 is transmitted before reflected by the touch body and using the anti-clockwise direction as the positive direction, the included angle between the e-axis direction of the first quarter-wave plate 111 and the polarization direction $P_0$ of the third linear polarizer 112 is −45°. Natural light emitted by the light-emitting unit 13 remains natural light after passing through the first quarter-wave plate 111. After passing through the third linear polarizer 112, the natural light becomes a linear polarized light that has a polarization direction same as the polarization direction $P_0$ of the third linear polarizer 112 and is located in a second quadrant and a fourth quadrant. Referring to FIG. 8B, after reflected by the touch body, the linear polarized light becomes the fingerprint signal light and remains linear polarized light with the unchanged polarization direction. However, facing the direction in which the fingerprint signal light is transmitted, the included angle between the e-axis direction of the first quarter-wave plate 111 and the polarization direction of the third linear polarizer 112 is 45°, and the fingerprint signal light is linear polarized light with the polarization direction in a first quadrant and a third quadrant. The fingerprint signal light has an unchanged polarization state and an unchanged light intensity when passing through the third linear polarizer 112 once again, and becomes levorotary circular polarized light and has an unchanged light intensity when passing through the first quarter-wave plate 111. The levorotary circular polarized light then becomes a linear polarized light that has a polarization direction in the second quadrant and the fourth quadrant and has an unchanged light intensity after passing through the second quarter-wave plate 221, and finally remains the linear polarized light that has an unchanged light intensity after passing through the fourth linear polarizer 222 that has a polarization direction parallel with the polarization direction of the linear polarized light. Referring to FIG. 9, a fingerprint noise light emitted from the organic light-emitting layer directly enters the second polarizer, and facing a direction in which the fingerprint noise light is transmitted, the included angle between the e-axis direction of the second quarter-wave plate 221 and the polarization direction $P_0$ of the fourth linear polarizer 222 is −45°. The fingerprint noise light remains natural light after passing through the second quarter-wave plate 221. After passing through the fourth linear polarizer 222, the natural light becomes a linear polarized light located in the second quadrant and the fourth quadrant that has a polarization direction same as the polarization direction $P_0$ of the fourth linear polarizer 222, and loses half of light intensity. Thus, the second polarizer can reduce the light intensity of the fingerprint noise light to improve the signal-to-noise ratio.

On the basis of the above-described solutions, optionally, it is possible to add an angle-defining film to the display panel so as to selectively filter out lights reflected onto a same fingerprint recognition unit by different positions of the touch body and thus to avoid interference caused by the light reflected by different positions of the touch body and irradiating the same fingerprint recognition unit, thereby improving the fingerprint recognition accuracy.

Figure 10A:
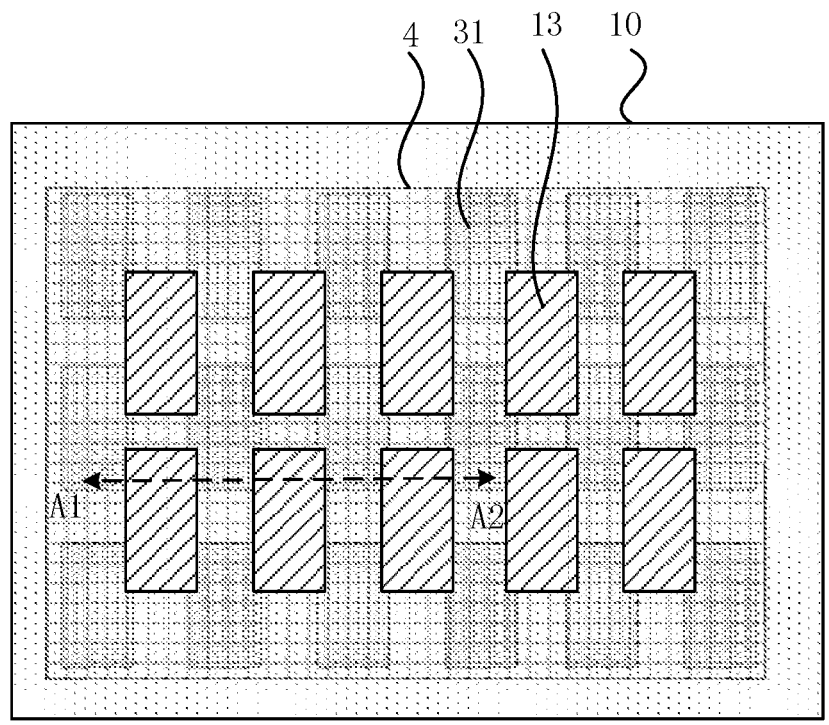
FIG. 10A is a top view of another display panel according to an embodiment of the present disclosure.
Figure 10B:
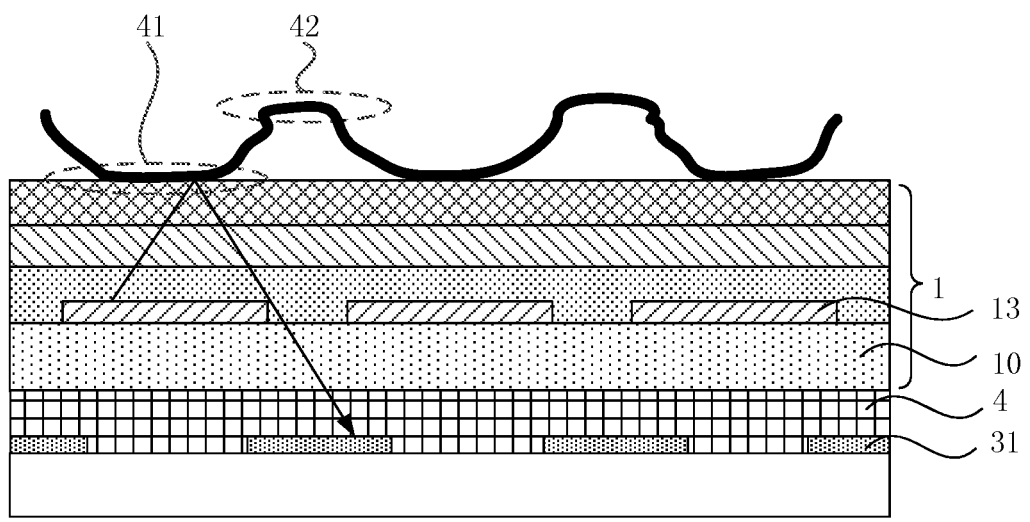
FIG. 10B is a cross sectional view taken along a line A1-A2 of FIG. 10A.

FIG. 10A is a top view of another display panel according to an embodiment of the present disclosure. FIG. 10B is a cross sectional view taken along a line A1-A2 of FIG. 10A. Referring to FIGS. 10A and 10B, the display panel includes a display module 1, fingerprint recognition units 31 and an angle-defining film 4. The display module 1 includes a substrate 10, and a plurality of light-emitting units 13 on the substrate 10. The fingerprint recognition units 31 are in a display area 11 on a side of the substrate 10 facing away from the light-emitting units 13. The angle-defining film 4 is between the display module 1 and the fingerprint recognition units 31.

The fingerprint recognition units 31 can perform fingerprint recognition according to light reflected onto the fingerprint recognition unit 31 by a touch body. The angle-defining film 4 can filter out lights having an incidence angle with respect to the angle-defining film 4 greater than a transmittance angle of the angle-defining film 4 from light reflected onto the fingerprint recognition unit 31 by the touch body. A transmittance of the angle-defining film 4 with respect to incident light perpendicular to the angle-defining film 4 may be set to f. The transmittance angle of the angle-defining film 4 refers to an incidence angle of light with a transmittance of k'*f with respect to the angle-defining film 4, where 0<k'<1. The light that has an incidence angle with respect to the angle-defining film 4 greater than the transmittance angle of the angle-defining film 4 can be filtered out by the angle-defining film 4. Optionally, k' may be set to 0.1. That is, the transmittance angle of the angle-defining film 4 refers to an incidence angle of light with a transmittance of 0.1f with respect to the angle-defining film 4.

The fingerprint recognition units 31 can perform fingerprint recognition according to the lights emitted from the light emitting unit 13 and then reflected onto the fingerprint recognition units 31 by the touch body, e.g., light indicated by a solid line illustrated in FIG. 10B. The angle-defining film 4 can filter out the light that has an incidence angle with respect to the angle-defining film 4 greater than the transmittance angle of the angle-defining film 4 from the light reflected onto the fingerprint recognition unit 31 by the touch body. This avoids interference caused by the lights emitted from the light-emitting unit 13, reflected by different positions of the touch body and then irradiating the same fingerprint recognition unit 31, thereby improving the fingerprint recognition accuracy of the fingerprint recognition unit 31.

Optionally, a transmittance of the light reflected by the touch body vertically and irradiating the fingerprint recognition unit 31 through the display module 1 is greater than 1%. Specifically, if the transmittance of the light reflected by the touch body vertically and irradiating the fingerprint recognition unit 31 through the display module 1 is too low when the fingerprint recognition unit 31 performs fingerprint recognition according to light emitted from the light-emitting unit 13, then light reaching the fingerprint recognition unit 31 has a low intensity, thus affecting the fingerprint recognition accuracy. Exemplarily, a thickness of each film through which the light passes may be adjusted so that the transmittance of the light reflected by the touch body vertically and irradiating the fingerprint recognition unit 31 through the display module 1 is adjusted.

Optionally, the display panel may include a light-emitting surface and a non-light-emitting surface. The light-emitting surface is on a side of the light-emitting units 13 facing away from the substrate 10. The non-light-emitting surface is on a side of the substrate 10 facing away from the light-emitting units 13. When the fingerprint recognition unit 31 performs fingerprint recognition according to the light emitted from the light emitting unit 13, a ratio of brightness of the light-emitting surface of the display panel to brightness of the non-light-emitting surface of the display panel may be greater than 10:1. Light emitted from the non-light-emitting surface of the display panel affects the process that the fingerprint recognition unit 31 performs fingerprint recognition according to the light emitted from the light emitting unit 13 and then reflected onto the fingerprint recognition unit 31 by the touch body, causing interferences in light detected by the fingerprint recognition unit 31. The fingerprint recognition accuracy will be seriously affected if the non-light-emitting surface of the display panel is over bright.

FIGS. 10A and 10B illustrate relative positions of the light-emitting units 13 and the fingerprint recognition units 31 by way of example. In the embodiment of the present disclosure, the relative positions of the light-emitting units 13 and the fingerprint recognition units 31 are not limited as along as light emitted from the light-emitting units 13 can be reflected onto the fingerprint recognition units 31 by the touch body.

Figure 11A:
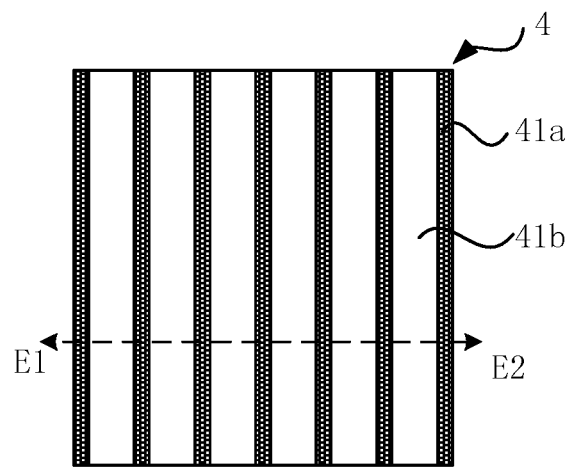
FIG. 11A is a top view of an angle-defining film according to an embodiment of the present disclosure.
Figure 11B:
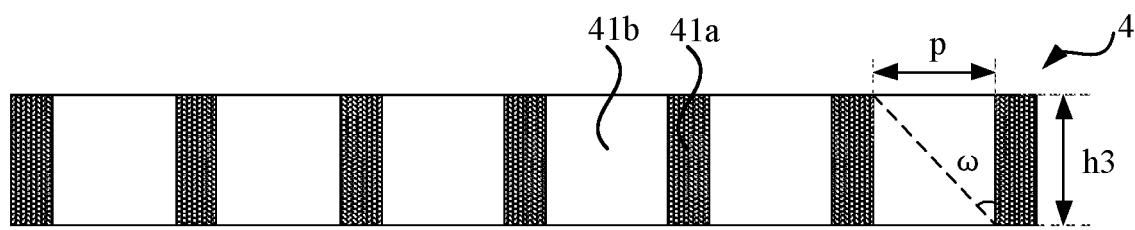
FIG. 11B is a cross sectional view taken along a line E1-E2 of FIG. 11A.

FIG. 11A is a top view of an angle-defining film according to an embodiment of the present disclosure. FIG. 11B is a cross sectional view taken along a line E1-E2 of FIG. 11A. Referring to FIGS. 11A and 11B, the angle-defining film 4 includes a plurality of light-proof areas 41a and a plurality of light-transmitting areas 41b arranged alternately in a same direction and extending in a direction perpendicular to a substrate 10. The light-proof areas 41a are provided with light-absorbing material.

Specifically, light irradiating the light-proof area 41a is absorbed by the light-absorbing material in the light-proof area 41a. That is, this part of light reflected by the touch body cannot pass through the angle-defining film 4 and then irradiate the fingerprint recognition unit 31 and the angle-defining film 4 can effectively filter out this part of light. As illustrated in FIG. 11B, since the light irradiating the light-proof area 41a is absorbed by the light-absorbing material in the light-proof area 41a, a transmittance angle of the angle-defining film 4 satisfies the following formula:

$$\omega = \arctan\frac{p}{h3}$$

In the formula, ω denotes the transmittance angle of the angle-defining film 4, p denotes a width of one light-transmitting area 41b in the direction the light-transmitting areas 41b are arranged, and h3 denotes a thickness of the angle-defining film 4. As can be seen from FIG. 11B, ω, p and h3 satisfy a formula $$\tan\omega = \frac{p}{h3},$$

so the transmittance angle of the angle-defining film 4 satisfies the preceding formula. Since the light irradiating the light-proof area 41a is absorbed by the light-absorbing material in the light-proof area 41a, the angle-defining film 4 filters out light that has an incidence angle with respect to the angle-defining film 4 greater than the calculated transmittance angle. The part of light does not need to be detected during fingerprint recognition, so such configurations of the angle-defining film 4 prevent the light that has an incidence angle with respect to the angle-defining film 4 greater than the transmittance angle of the angle-defining film 4 from being transmitted to the fingerprint recognition unit 31 and from causing interferences to fingerprint recognition.

Optionally, when the angle-defining film 4 includes multiple light-proof areas 41a and multiple light-transmitting areas 41b arranged alternately in the same direction and extending in the direction perpendicular to the substrate 10 and the light-proof areas 41a are provided with light-absorbing material, a light diffusion distance of the angle-defining film 4 satisfies the following formula:

$$\Delta X = \frac{p(H3 + h3)}{h3}$$

In the formula, ΔX denotes the light diffusion distance of the angle-defining film 4 and H3 denotes a thickness of a display module 1. The light diffusion distance of the angle-defining film 4 refers to a distance between a reflection point of actual detection light and a reflection point of interference detection light on the touch body 40, where the actual detection light and the interference detection light correspond to the same fingerprint recognition unit 31. The actual detection light refers to the reflected light that has a smallest incidence angle with respect to the fingerprint recognition unit 31. The interference detection light refers to the reflected light that has an incidence angle with respect to the fingerprint recognition unit 31 greater than the incidence angle of the actual detection light and with respect to the fingerprint recognition unit 31.

Figure 11C:
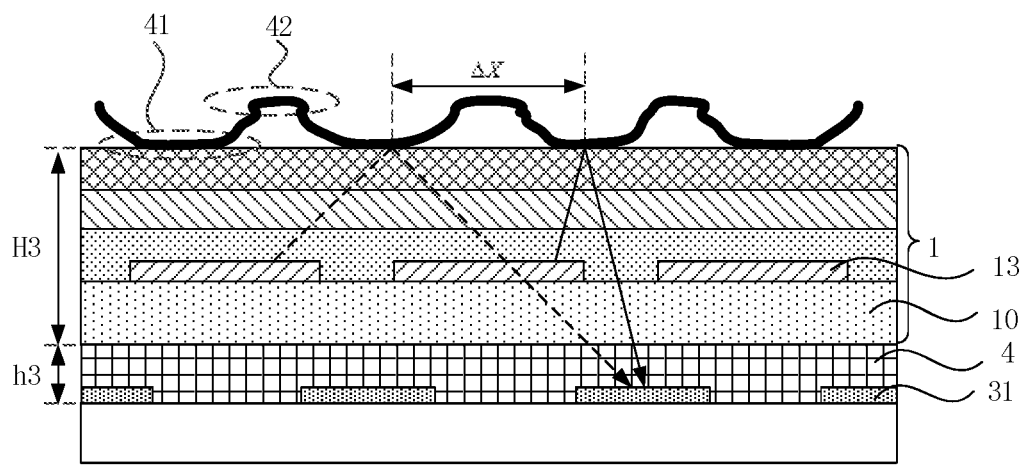
FIG. 11C is a cross sectional view of another display panel according to an embodiment of the present disclosure.

FIG. 11C illustrates an example in which the fingerprint recognition unit 31 performs fingerprint recognition according to the light emitted from the light emitting unit 13 and then reflected onto the fingerprint recognition unit 31 by the touch body. The light indicated by a solid arrow in FIG. 11C may be the reflected light (i.e., actual detection light) that has the smallest incidence angle with respect to the fingerprint recognition unit 31, and the light indicated by a dotted arrow may be reflected the light (i.e., interference detection light) that has an incidence angle with respect to the fingerprint recognition unit 31 greater than the incidence angle of the actual detection light and with respect to the fingerprint recognition unit 31. If the angle-defining film 4 is not provided, after reflected by different positions, e.g., two adjacent ridges 41, of the touch body, the two lights irradiate the same fingerprint recognition unit 31, i.e., interference occurs during fingerprint recognition.

Figure 11D:
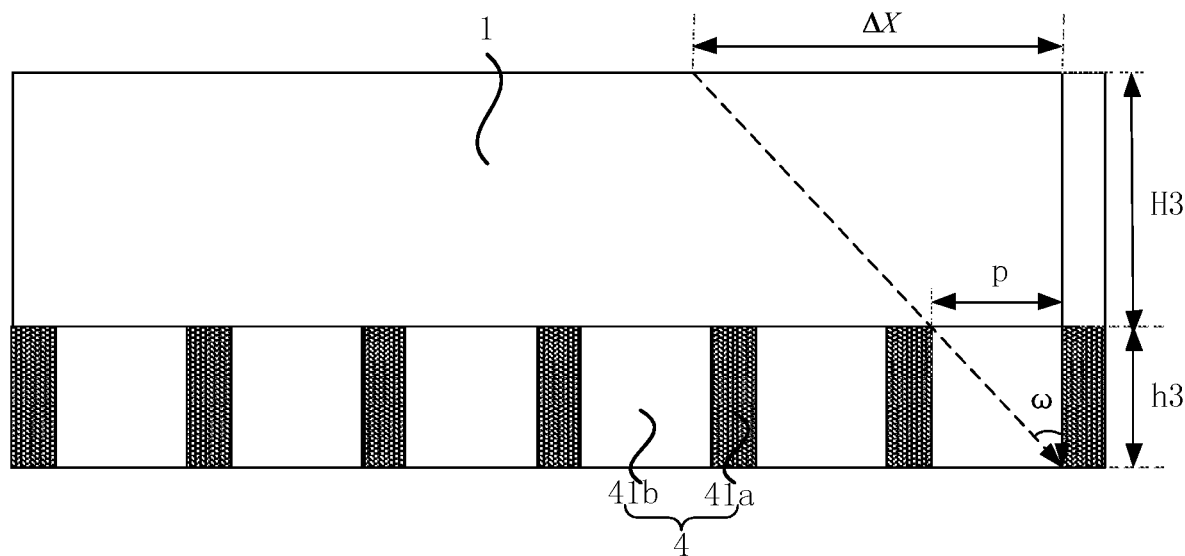
FIG. 11D is a diagram illustrating a geometric relationship of a light diffusion distance in the angle-defining film of FIG. 11A.

In this case, the light diffusion distance of the angle-defining film 4 is the distance between the reflection point of the actual detection light on the touch body and the reflection point of the interference detection light on the touch body. FIG. 11D illustrates an example in which the incidence angle of the actual detection light and with respect to the fingerprint recognition unit 31 is approximately 0°. In the example, among the incidence angles of the interference lights that can pass through the angle-defining film 4, the smallest incidence angle with respect to the fingerprint recognition unit 31 may be the transmittance angle of the angle-defining film 4. Therefore, $$\tan\omega = \frac{p}{h3} = \frac{\Delta X}{H3 + h3}$$

applies, and the light diffusion distance of the angle-defining film 4 satisfies this formula. The longer the light diffusion distance of the angle-defining film 4, the lower the fingerprint recognition accuracy of the display panel.

Figure 11E:
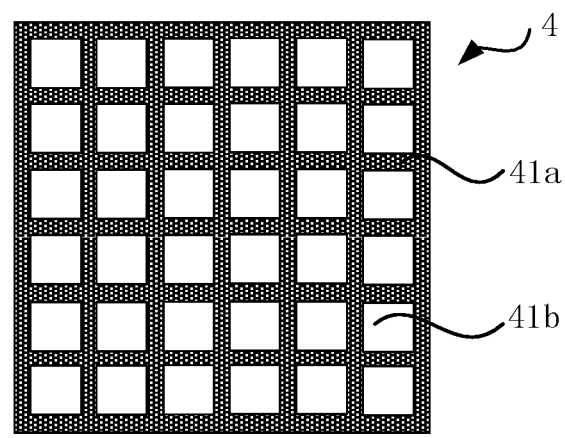
FIG. 11E is a top view of another angle-defining film according to an embodiment of the present disclosure.

FIG. 11A illustrates an example in which the angle-defining film 4 is configured as a one-dimensional structure, and the light-proof areas 41a and the light-transmitting areas 41b are arranged alternately in a horizontal direction in FIG. 11A. The angle-defining film 4 may also be configured as a two-dimensional structure as illustrated in FIG. 11E in which the light-proof areas 41a and the light-transmitting areas 41b may be arranged alternately in diagonal directions of the angle-defining film 4 of FIG. 11E. Compared with the angle-defining film 4 having a one-dimensional structure, the angle-defining film 4 having a two-dimensional structure can selectively filter out light incident on the angle-defining film 4 in various directions.

Figure 12A:
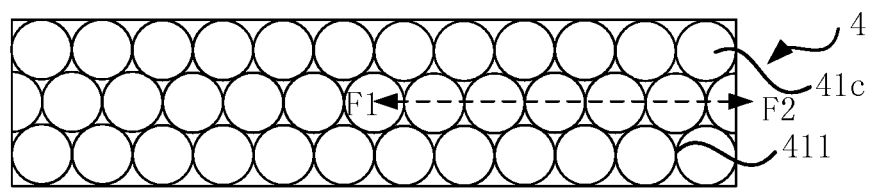
FIG. 12A is a top view of another angle-defining film according to an embodiment of the present disclosure.
Figure 12B:
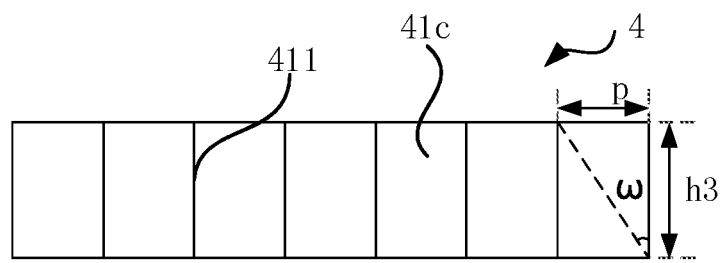
FIG. 12B is a cross sectional view taken along a line F1-F2 of FIG. 12A.

FIG. 12A is a top view of another angle-defining film according to an embodiment of the present disclosure. FIG. 12B is a cross sectional view taken along a line F1-F2 of FIG. 12A. Referring to FIGS. 12A and 12B, the angle-defining film includes a porous structure 41c. Side walls 411 of the porous structure 41c can absorb lights incident on the side walls 411. That is, such lights cannot irradiate the fingerprint recognition units 31. By way of example, the porous structures 41c may be glass-capillary structures. The side walls 411 of the glass capillaries may be coated with a black light-absorbing material so that the side walls 411 can absorb the lights incident on the side walls 411 and thus the angle-defining film 4 can filter out such lights. Optionally, light-absorbing material may be provided between adjacent porous structures 41c, or not be provided between adjacent porous structures 41c.

Specifically, since the side walls 411 of the porous structure 41c can absorb the light incident on the side walls 411, a transmittance angle of the angle-defining film 4 satisfies the following formula:

$$\omega = \arctan\frac{p}{h3}$$

In the formula, ω denotes the transmittance angle of the angle-defining film 4, p denotes a diameter of the porous structure 41c, and H3 denotes a thickness of the angle-defining film 4. As can be seen from FIG. 12B, ω, p and h3 satisfy a formula $$\tan\omega = \frac{p}{h3},$$

so the transmittance angle of the angle-defining film 4 satisfies the preceding formula.

Optionally, when the angle-defining film 4 includes the porous structure 41c and the side walls 411 of the porous structure 41c can absorb light incident on the side walls 411, a light diffusion distance of the angle-defining film 4 satisfies the following formula:

$$\Delta X = \frac{p(H3+h3)}{h3}$$

In the formula, ΔX denotes the light diffusion distance of the angle-defining film 4 and H3 denotes a thickness of a display module 1. A derivation process of this formula is similar to a derivation process of the light diffusion distance of the angle-defining film 4 of the structure illustrated in FIG. 11A and thus will not be described herein. Similarly, the longer the light diffusion distance of the angle-defining film 4, the lower the fingerprint recognition accuracy of the display panel.

Figure 12C:
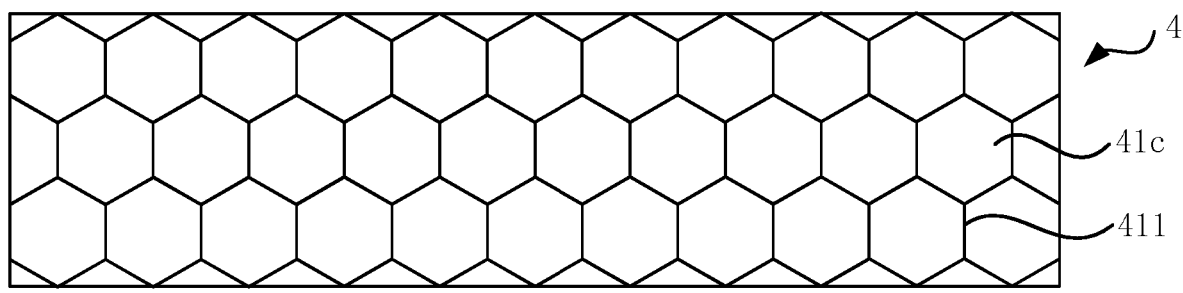
FIG. 12C is a top view of another angle-defining film according to an embodiment of the present disclosure.

When the angle-defining film 4 is viewed from the top, the porous structure 41c may be shaped as circles showed in FIG. 12A or hexagons showed in FIG. 12C. The shape of the porous structure 41c is not limited in the embodiment of the present disclosure.

Figure 13A:
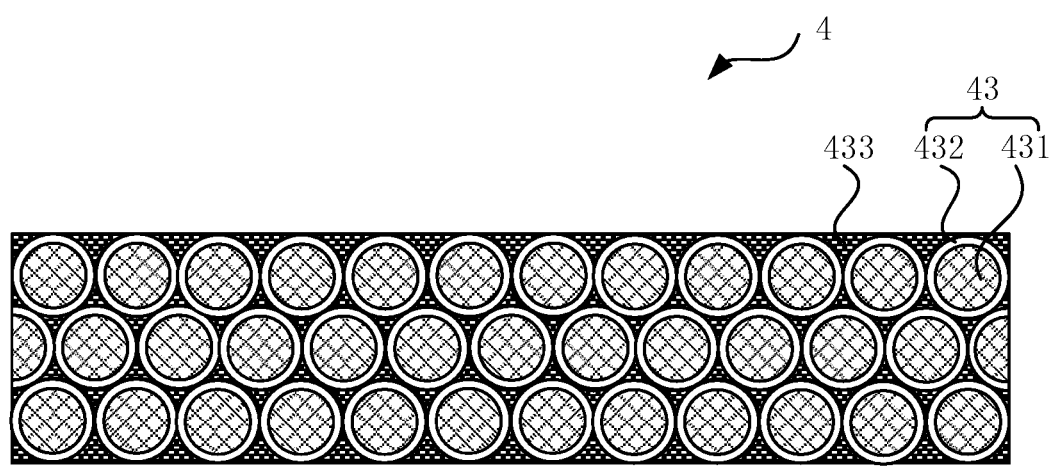
FIG. 13A is a top view of another angle-defining film according to an embodiment of the present disclosure.
Figure 13B:
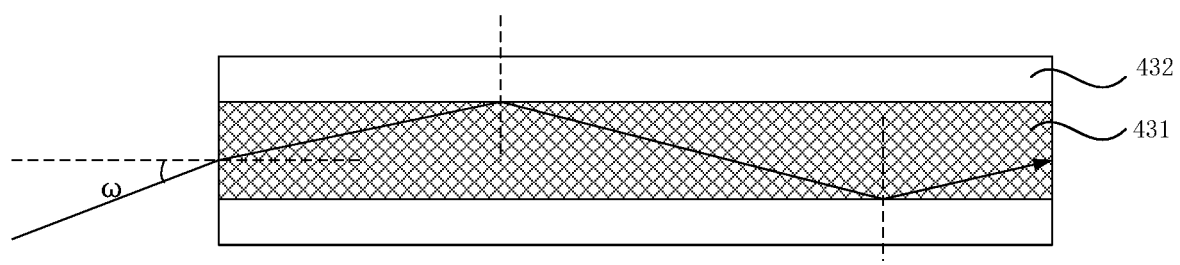
FIG. 13B is a cross sectional view taken along an extending direction of an optical fiber structure of FIG. 13A.

FIG. 13A is a top view of another angle-defining film according to an embodiment of the present disclosure. As illustrated in FIG. 13A, the angle-defining film 4 includes a plurality of optical fiber structures 43 arranged in a same direction. FIG. 13B is a cross sectional view taken along an extending direction of the optical fiber structure 43 of FIG. 13A. Referring to FIGS. 13A and 13B, the optical fiber structure 43 includes a core 431 and a cladding 432, and light-absorbing material 433 is provided between every two adjacent optical fiber structures 43, so that lights which go through the optical fiber structure 43 to the space between two optical fiber structures 43 can be absorbed by the light-absorbing material 433 between the two optical fiber structures 43 and thus the angle-defining film 4 can filter out such lights.

Specifically, the core 431 and the cladding 432 of the optical fiber structure 43 have different refractive indexes, and a transmittance angle of the angle-defining film 4 satisfies the following formula:

$$n\cdot\sin\omega = \sqrt{n_{core}^2 - n_{clad}^2}$$

In the formula, ω denotes the transmittance angle of the angle-defining film 4, n denotes a refractive index of a film of the display module 1 in contact with the angle-defining film 4, $n_{core}$ denotes a refractive index of the core 431 of the optical fiber structure 43, and $n_{clad}$ denotes a refractive index of the cladding 432 of the optical fiber structure 43. As illustrated in FIG. 13B, when an incidence angle of the light reflected by a touch body with respect to the angle-defining film 4 composed of the optical fiber structures 43 is greater than ω, this light does not undergo total reflection in the optical fiber structure 43. That is, this light can penetrate through the optical fiber structure 43 and be absorbed by the light-absorbing material between the optical fiber structures 43. That is, this light can be filtered out by the angle-defining film 4 and thus cannot be incident on the fingerprint recognition unit 31. This enables the angle-defining film 4 to filter out light that has an incidence angle with respect to the angle-defining film 4 greater than the transmittance angle of the angle-defining film 4 and avoids interference caused by backlight 3 reflected by different positions of the touch body and then incident on the same fingerprint recognition unit 31, thereby improving the fingerprint recognition accuracy.

Optionally, when the angle-defining film 4 includes multiple optical fiber structures 43 arranged in the same direction, the core 431 and the cladding 432 of the optical fiber structure 43 have different refractive indexes, and the light-absorbing material 433 is provided between every two adjacent optical fiber structures 43, a light diffusion distance of the angle-defining film 4 satisfies the following formula:

$$\Delta X = H3 \cdot \tan\omega.$$

Figure 13C:
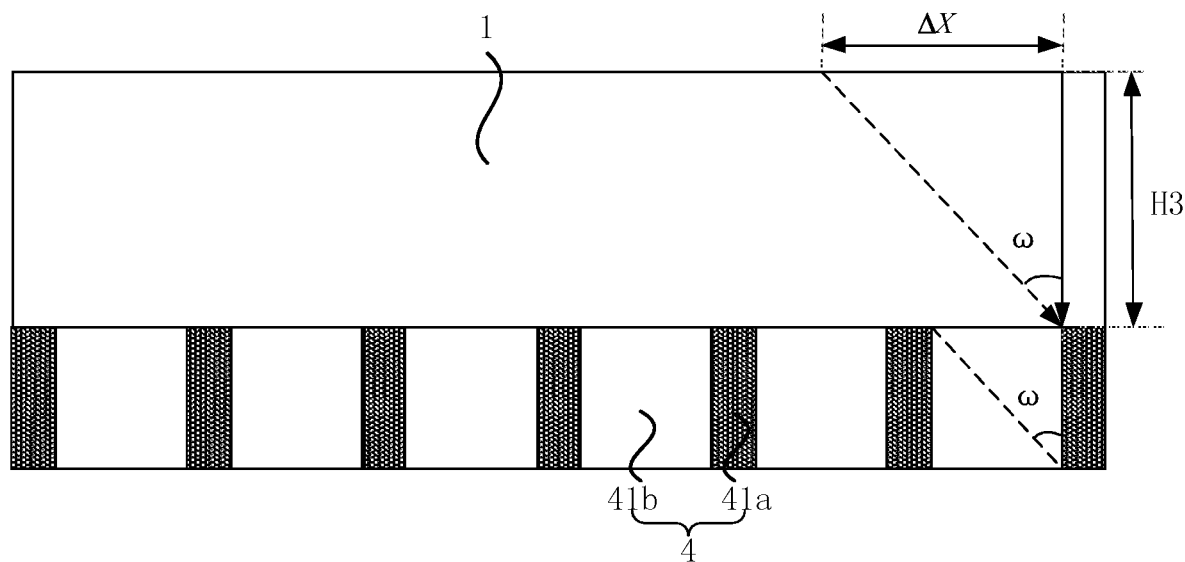
FIG. 13C is a diagram illustrating a geometric relationship of a light diffusion distance in the angle-defining film of FIG. 13A.

In the formula, ΔX denotes the light diffusion distance of the angle-defining film 4 and H3 denotes a thickness of the display module 1. FIG. 13C illustrates an example in which an incidence angle of the actual detection light with respect to the fingerprint recognition unit 31 is approximately 0°. In the example, among interference lights that can pass through the angle-defining film 4, the smallest incidence angle with respect to the fingerprint recognition unit 31 may be the transmittance angle of the angle-defining film 4, i.e., a threshold of an incidence angle that allows the light to undergo total reflection in the optical fiber structure 43. Thus a formula $$\tan\omega = \frac{\Delta X}{H3}$$

applies. Similarly, the longer the light diffusion distance of the angle-defining film 4, the lower the fingerprint recognition accuracy of the display panel.

Figure 14A:
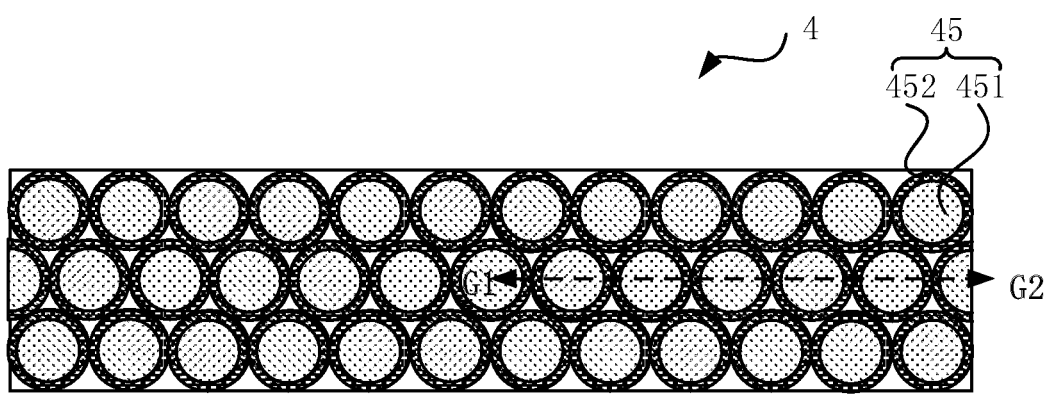
FIG. 14A is a top view of another angle-defining film according to an embodiment of the present disclosure.
Figure 14B:
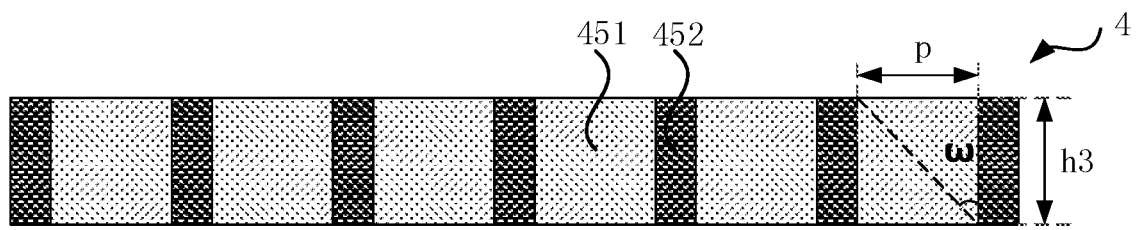
FIG. 14B is a cross sectional view taken along a line G1-G2 of FIG. 14A.

FIG. 14A is a top view of another angle-defining film according to an embodiment of the present disclosure. FIG. 14B is a cross sectional view taken along a line G1-G2 of FIG. 14A. Referring to FIGS. 14A and 14B, the angle-defining film 4 includes a plurality of columnar structures 45 arranged in a same direction, and each columnar structure 45 includes a core 451 and a cladding 452. The core 451 and the cladding 452 have a same refractive index. Material of the cladding 452 includes light-absorbing material, so that light incident on the cladding 452 after passing through the core 451 can be absorbed by the cladding 452, i.e., this light cannot be incident on the fingerprint recognition unit 31. Optionally, light-absorbing material may be provided between adjacent columnar structures 45 or may not be provided between adjacent columnar structures 45.

Specifically, the light incident on the cladding 452 after passing through the core 451 can be absorbed by the cladding 452, and therefore a transmittance angle of the angle-defining film 4 satisfies the following formula:

$$\omega = \arctan\frac{p}{h3}$$

In the formula, ω denotes the transmittance angle of the angle-defining film 4, p denotes a diameter of the core 451, and h3 denotes a thickness of the angle-defining film 4. As can be seen from FIG. 14B, ω, p and h3 satisfy a formula $$\tan\omega = \frac{p}{h3},$$

so the transmittance angle of the angle-defining film 4 satisfies the preceding formula.

Optionally, when the angle-defining film 4 includes multiple columnar structures 45 arranged in the same direction, each columnar structure 45 includes the core 451 and the cladding 452, the core 451 and the cladding 452 have the same refractive index, and the material of the cladding 452 includes light-absorbing material, the light diffusion distance of the angle-defining film 4 satisfies the following formula:

$$\Delta X = \frac{p \cdot (H3 + h3)}{h3}$$

In the above formula, ΔX denotes the light diffusion distance of the angle-defining film 4 and H3 denotes a thickness of a display module 1. A derivation process of this formula is similar to a derivation process of the light diffusion distance of the angle-defining film 4 of the structure illustrated in FIG. 11A and thus will not be described herein. Similarly, the longer the light diffusion distance of the angle-defining film 4, the lower the fingerprint recognition accuracy of the display panel.

When the angle-defining film 4 is viewed from the top, the columnar structure 45 may be shaped as circles illustrated in FIG. 14A or another shape. The shape of the columnar structure 45 is not limited in the embodiment of the present disclosure.

Optionally, the angle-defining film 4 has a light diffusion distance less than 400 μm. In this case, the larger the light diffusion distance of the angle-defining film 4, the longer a distance between the reflection point of actual detection light on a touch body and the reflection point of interference detection light on a touch body. If the distance between the reflection point of the actual detection light and the reflection point of the interference detection light on the touch body is greater than a distance between a valley 42 and an adjacent ridge 41 of a fingerprint, errors will occur in a fingerprint recognition process of the display panel and fingerprint recognition cannot be performed, seriously affecting the fingerprint recognition accuracy of the display panel.

According to the embodiments, the light-emitting units 13 serve as light sources for the fingerprint recognition units 31 and lights emitted from the light-emitting units 13 are reflected by the touch body and then transmitted into the fingerprint recognition unit 31 so that fingerprint recognition is performed. In the fingerprint recognition stage, it may be configured such that only one light-emitting unit 13 within a range twice the light diffusion distance of the angle-defining film 4 emits light. Such configurations greatly reduce a probability that lights emitted from different light-emitting units 13 are reflected by different positions of the touch body and then transmitted into a same fingerprint recognition unit 31 and thus reduce a probability of interference caused by the lights emitted from the light-emitting units 13, reflected by different positions of the touch body and then transmitted into the same fingerprint recognition unit 31, thereby improving fingerprint recognition accuracy.

Optionally, an optical adhesive layer may be disposed between fingerprint recognition units 31 and the angle-defining film 4 for bonding the fingerprint recognition units 31 to the angle-defining film 4.

In the embodiment of the present disclosure, the angle-defining film 4 is disposed between the display module 1 and the fingerprint recognition units 31 and is capable of effectively filtering out the lights that have an incidence angle with respect to the angle-defining film 4 greater than the transmittance angle of the angle-defining film 4 from the lights reflected onto the fingerprint recognition unit 31 by the touch body. That is, the angle-defining film 4 can selectively filter out the lights reflected onto the same fingerprint recognition unit 31 by different positions of the touch body. This avoids interference caused by the lights reflected by different positions of the touch body and incident on the same fingerprint recognition unit 31, thereby improving the fingerprint recognition accuracy.

In an existing display device with a fingerprint recognition function, after reflected by a finger, the lights emitted from a light source for fingerprint recognition are incident onto multiple fingerprint recognition units. Each fingerprint recognition unit receives interference signals from other positions in addition to a fingerprint signal from a position corresponding to the respective fingerprint recognition unit. This affects fingerprint recognition accuracy. To solve the above problem, the present disclosure provides solutions below.

Figure 15A:
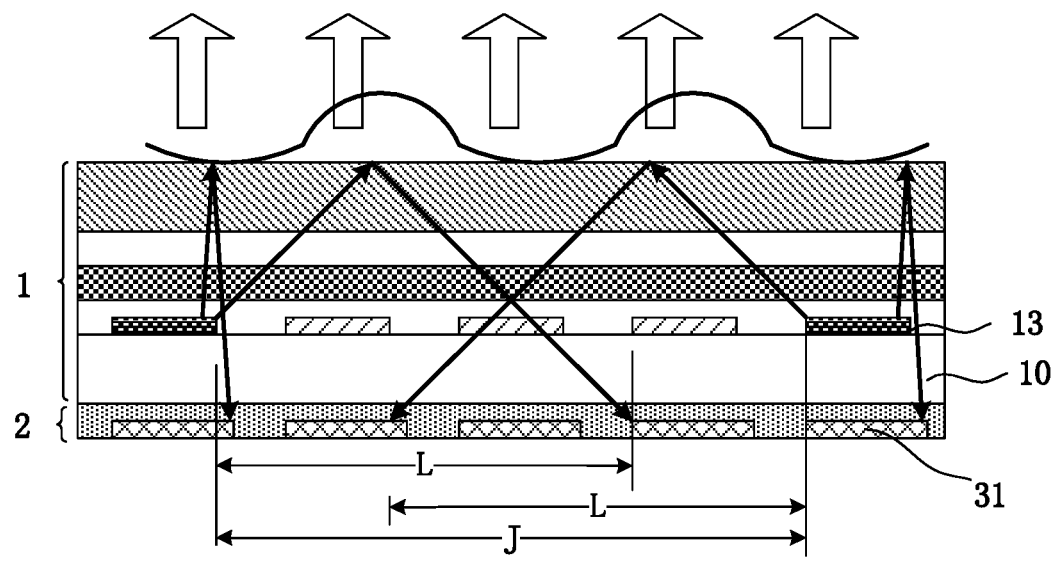
FIG. 15A is a schematic diagram of another display panel according to an embodiment of the present disclosure.
Figure 15B:
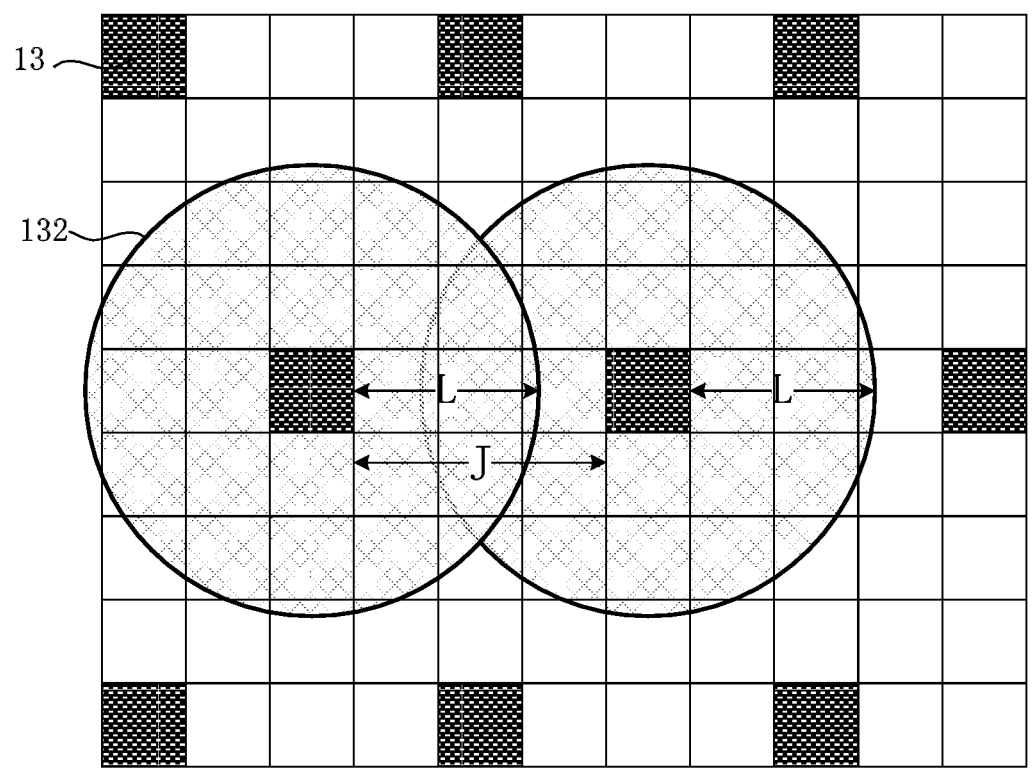
FIG. 15B is a partial top view of the display panel of FIG. 15A.
Figure 15C:
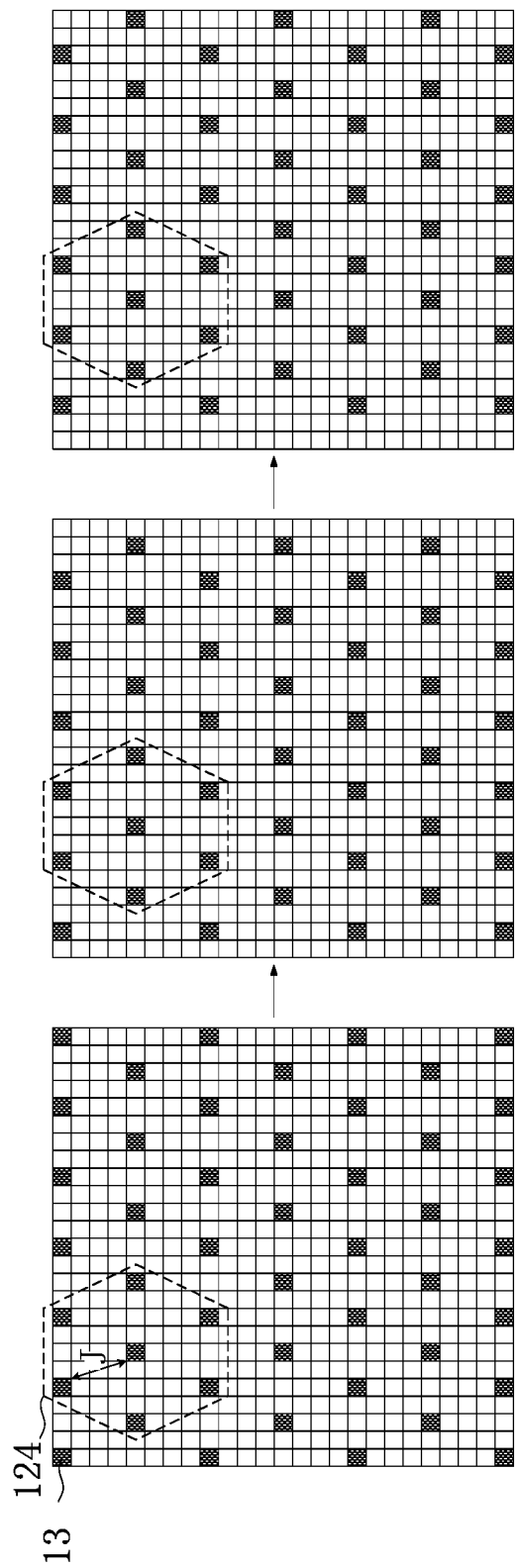
FIG. 15C is a scanning diagram of the display panel of FIG. 15A in a fingerprint recognition stage.

FIG. 15A is a structural diagram of another display panel according to an embodiment of the present disclosure. FIG. 15B is a partial top view of the display panel of FIG. 15A. FIG. 15C is a scanning diagram of the display panel of FIG. 15A in a fingerprint recognition stage. The display panel provided by the embodiment of the present disclosure includes a display module 1 and a fingerprint recognition module 2. The display module 1 includes a substrate 10, and a plurality of light-emitting units 13 on a side of the substrate 10. The fingerprint recognition module 2 includes fingerprint recognition units 31. A side of the light-emitting unit 13 facing away from the substrate 10 is a light-emitting surface of the display panel. In the fingerprint recognition stage, the light-emitting units 13 emit light according to a first light-emitting dot array 124 in a shifting manner. A distance J between any two adjacent light-emitting units 13 in the first light-emitting dot array 124 is greater than or equal to a minimum non-interference distance L. The minimum non-interference distance L refers to a maximum radius of a coverage area 132 formed by light emitted from any light-emitting unit 13 and then reflected onto the display panel by a touch body. Optionally, each fingerprint recognition unit 31 corresponds to a respective light-emitting unit 13 in the present embodiment.

Figure 16:
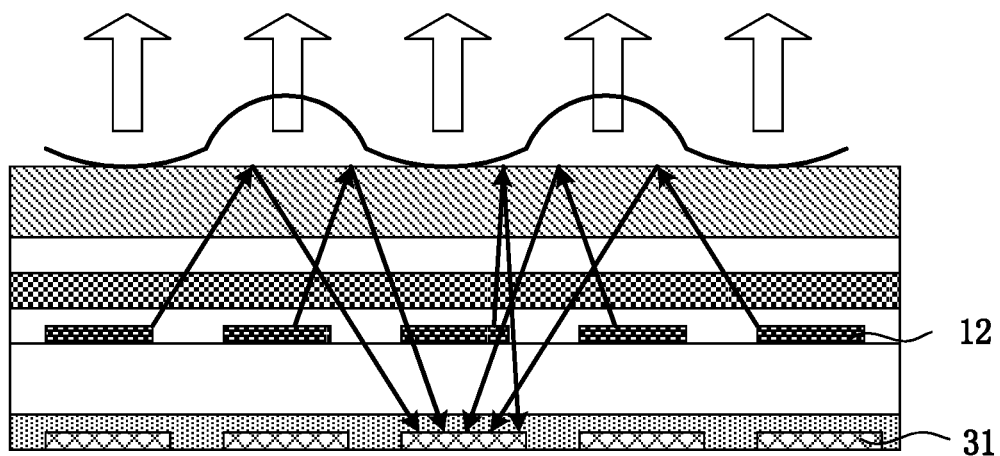
FIG. 16 is a diagram illustrating light path interference of various reflected light by the touching object inside a display panel.

The display panel provided by the embodiment of the present disclosure uses the display module 1 as the light source for fingerprint recognition. Specifically, the light-emitting units 13 in the display module 1 serve as light sources for fingerprint recognition of the fingerprint recognition units 31. When a user's finger presses against the light-emitting surface of the display panel, lights emitted from a light-emitting unit 13 irradiate the user's finger, then is reflected by a fingerprint of the user to form the reflected light and incident on the fingerprint recognition unit 31 corresponding to the light-emitting unit 13 from the light-emitting surface of the display panel. Upon receiving the fingerprint signal light, the fingerprint recognition unit 31 produces an inductive signal. A fingerprint recognition circuit of the display panel may perform fingerprint recognition according to the inductive signal. A reason why the first light-emitting dot array 124 is used as a detection light source of the fingerprint recognition unit 31 is that the lights emitted from the light-emitting unit 13 have a wide range of angular distribution. As illustrated in FIG. 16, if all the light-emitting units 13 of the display panel emit light simultaneously when fingerprint recognition is performed, then each fingerprint recognition unit 31 receives interference signals from other light-emitting units 13 in addition to the fingerprint signal light from the corresponding light-emitting unit 13. This reduces fingerprint recognition accuracy.

To increase the fingerprint recognition accuracy, in the display panel provided in the present embodiment, the plurality of light-emitting units 13 emit light according to the first light-emitting dot array 124 in a shifting manner in the fingerprint recognition stage. The distance J between any two adjacent light-emitting units 13 in the first light-emitting dot array 124 is greater than or equal to the minimum non-interference distance L. As illustrated in FIGS. 15A and 15B, the lights emitted from the light-emitting unit 13 have an angular distribution, so, after being reflected by the touch body, the lights emitted from the light-emitting unit 13 forms a coverage area 132 in the display panel, and the fingerprint signal lights of the lights emitted from the light-emitting unit 13 at any angle falls within the respective coverage area 132. The maximum radius of the coverage area 132 is the minimum non-interference distance L. In the present embodiment, the distance J between any two adjacent light-emitting units 13 in the first light-emitting dot array 124 is greater than or equal to the minimum non-interference distance L, so the fingerprint signal light of each light-emitting unit 13 is not incident onto the fingerprint recognition units 31 corresponding to other light-emitting units 13 that emit light at the same time. That is, the fingerprint recognition unit 31 corresponding to each light-emitting unit 13 in the first light-emitting dot array 124 receives only the fingerprint signal light of the corresponding light-emitting unit 13. Therefore, in the display panel provided by the present embodiment, the fingerprint recognition unit 31 does not receive interference signals from other light-emitting units. Accordingly, the fingerprint recognition circuit of the display panel performs fingerprint recognition according to the inductive signal produced by the fingerprint recognition unit 31, thus increasing the fingerprint recognition accuracy of the display panel.

The fingerprint signal light refers to the reflected light formed by reflection of the light emitted from the light-emitting unit 13 by the user's fingerprint pressing against the display panel. In contrast to a thickness of the display panel, a distance between the user's fingerprint and the light-emitting surface of the display panel is small and thus has little impact on a range of the coverage area 132. Therefore, a reflection distance between the user's finger and the light-emitting surface of the display panel is omitted when the minimum non-interference distance L is calculated in the present embodiment. Furthermore, in theory, the radius L of the coverage area 132 should be calculated with a center point of the light-emitting unit 13 as an origin. However, in practice, the number of the light-emitting units 13 in the display panel is very large, and the sizes of each light-emitting unit 13 are very small contrast to the large number of light-emitting units 13 in the display panel. Therefore, in the present embodiment, the light-emitting unit 13 as a whole may be seen as the origin of the coverage area 132, so the radius L of the coverage area 132 may be denoted as a distance from an edge of the light-emitting unit 13 to an edge of the corresponding coverage area 132, and the sizes of the light-emitting unit 13 may be excluded from the calculation of the minimum non-interference distance L. It is to be understood by those skilled in the art that the minimum non-interference distance L is related to the thickness of the display panel and a light-emitting angle of the light-emitting unit, etc. Therefore, different display panels have different minimum non-interference distances L. The sizes of the light-emitting unit may be included in the minimum non-interference distance L in other optional embodiments. This is not limited in the present disclosure.

As described above, the lights emitted from the light-emitting unit 13 have an angular distribution, and the minimum non-interference distance L refers to the maximum radius of the coverage area 132 formed by lights emitted from the light-emitting unit 13 and then reflected onto a fingerprint recognition layer 21. Apparently, an area defined by the reflected light with a maximum angle among the lights emitted from an edge of the light-emitting unit 13 is the coverage area 132, and the reflected lights of the lights emitted at any angle from the edge of the light-emitting unit 13 fall within the coverage area 132.

Figure 15D:
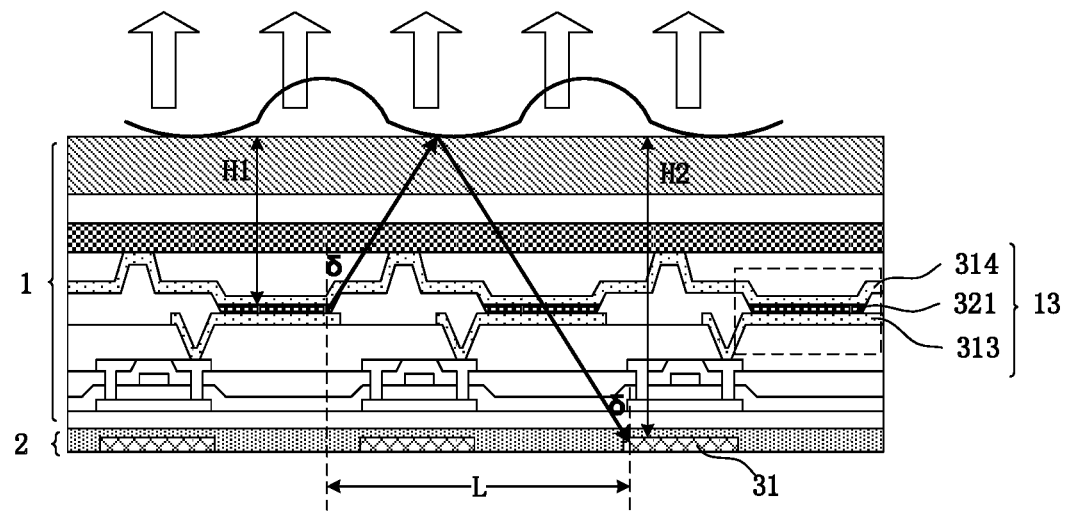
FIG. 15D is a cross sectional diagram of FIG. 15A.

As illustrated in FIG. 15D, in the embodiment of the present disclosure, each light-emitting unit 13 includes an anode 313, a light-emitting function layer 321 and a cathode 314 in sequence in a direction perpendicular to the substrate 10. One anode 313, one light-emitting function layer 321 corresponding to the anode 313 and one cathode 314 corresponding to the anode 313 form one light-emitting unit 13. Optionally, each light-emitting unit 13 includes light-emitting sub-units in three colors. The light-emitting function layer 321 emits light when signals are applied to the anode 313 and the cathode 314. The lights emitted from the light-emitting function layer 321 have an angular distribution. A fingerprint-reflected signal substantially belongs to specular reflection and a reflection angle is equal to an incidence angle, so a formula $L = \tan \delta \times H1 + \tan \delta \times H2$ applies. L denotes the minimum non-interference distance and $\delta$ denotes an included angle between a direction corresponding to preset brightness of the light-emitting unit 13 and a direction perpendicular to an organic light-emitting layer. H1 denotes a height from the light-emitting surface of the display panel to the light-emitting function layer 321 in the direction perpendicular to the display panel, and H2 denotes a height from the light-emitting surface of the display panel to the fingerprint recognition 31 in the direction perpendicular to the display panel. The preset brightness is less than or equal to 10% of brightness in a direction perpendicular to the organic light-emitting layer.

In the present embodiment, the angle of the light emitted from the light-emitting unit 13 is related to brightness of the light-emitting unit 13, and the brightness is a subjective perception of a (achromatic) light intensity. In the present embodiment, the brightness of the light-emitting unit 13 in a perpendicular direction is defined as 100%. The lower the brightness percentage, the larger the corresponding light-emitting angle (i.e., included angle with a direction perpendicular to the light-emitting function layer 321) and accordingly the weaker the light intensity. When the brightness of the light-emitting unit 13 is less than or equal to 10%, the intensity of the light emitted from the light-emitting unit 13 is weak, and the reflected light formed on the light-emitting surface of the display panel does not bring about interference to the fingerprint recognition unit 31. Therefore, the light-emitting angle of the light-emitting unit 13 is set to a value corresponding to the brightness threshold of 10% in the present embodiment. On this basis, a process of determining δ is: measuring the brightness of the light-emitting unit 13 in the perpendicular direction, determining the position corresponding to 10% of the brightness in the direction perpendicular to the light-emitting layer, and then determining δ based on the included angle between the direction of this position and the direction perpendicular to the organic light-emitting layer. It is to be understood by those skilled in the art that light-emitting units of different display panels may have different light intensities and different preset brightness values. For example, in other optional embodiments, the preset brightness value may be optionally 12% or 9% of the brightness in the direction perpendicular to the organic light-emitting layer, and is not limited in the present disclosure.

FIG. 15C is a scanning diagram of the display panel. The display panel performs fingerprint recognition using a picture scanning mode in the fingerprint recognition stage. Specifically, multiple light-emitting units 13 emit light simultaneously according to the first light-emitting dot array 124 and inductive signals produced by the fingerprint recognition units 31 corresponding to the light-emitting units 13 which are emitting light are recorded. In a next picture, light-emitting units 13 simultaneously emitting light are shifted and the corresponding inductive signals are recorded until all light-emitting units 13 emit light successively, and fingerprint recognition is performed according to the obtained inductive signals of the fingerprint recognition units 31. Since the fingerprint recognition units 31 of the present embodiment do not receive interference signals, the fingerprint recognition accuracy of the present embodiment is high. It is to be understood by those skilled in the art that the first light-emitting dot array may be a minimum repetitive unit composed of multiple light-emitting units that emit light simultaneously, and is not limited to a dot array formed by multiple light-emitting units that emit light simultaneously.

In the display panel provided by the embodiment of the present disclosure, multiple light-emitting units emit light according to the first light-emitting dot array in a shift manner in the fingerprint recognition stage. A distance between any two adjacent light-emitting units in the first light-emitting dot array is greater than or equal to the minimum non-interference distance. The minimum non-interference distance L refers to the maximum radius of the coverage area formed by lights emitted from the light-emitting unit and then reflected onto the fingerprint recognition array. Apparently, the fingerprint signal light of any light-emitting unit in the first light-emitting dot array is not incident onto the fingerprint recognition units corresponding to other light-emitting units that emit light at the same time. That is, the fingerprint recognition unit corresponding to each light-emitting unit in the first light-emitting dot array receives only the fingerprint signal light of the corresponding light-emitting unit. Therefore, the fingerprint recognition unit does not receive interference signals from other light-emitting units. Accordingly, the fingerprint recognition circuit of the display panel performs fingerprint recognition according to the inductive signal produced by the fingerprint recognition unit, thus increasing the fingerprint recognition accuracy of the display panel.

FIG. 15A illustrates the structure of one display panel of the present disclosure. Display panels with other structures are provided in other embodiments of the present disclosure.

Figure 17A:
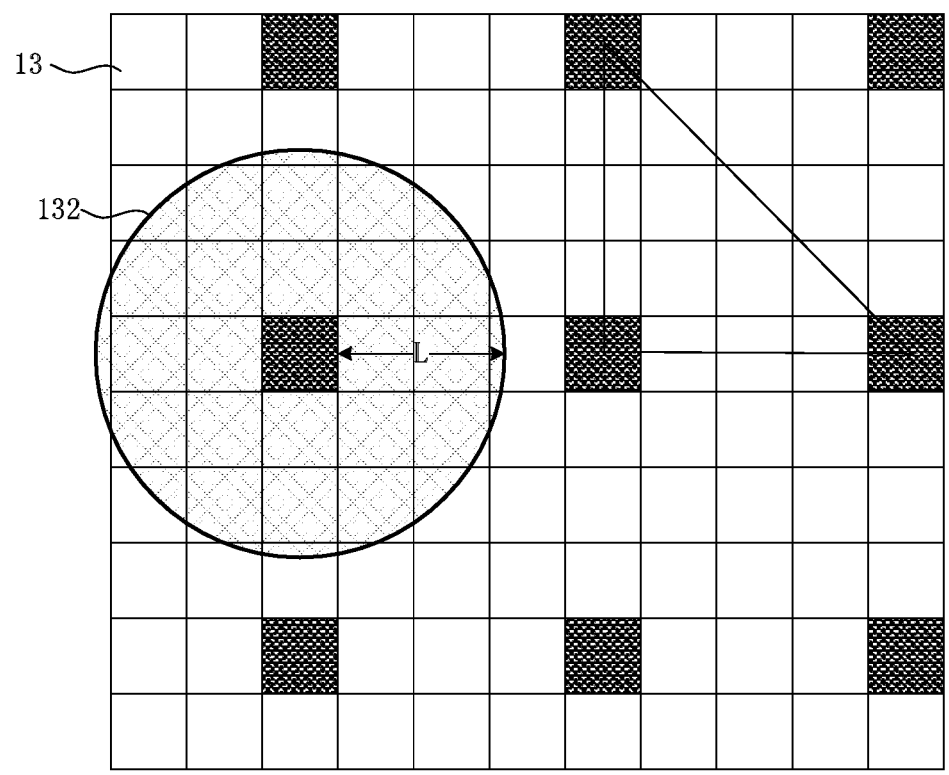
FIGS. 17A and 17B are respective scanning diagrams of other two display panels in fingerprint recognition stages according to embodiments of the present disclosure.

When the display panel reads fingerprint information in the picture scanning mode, in one frame of picture, multiple light-emitting units 13 emit light according to the first light-emitting dot array 124 and the fingerprint information of the fingerprint recognition units 31 corresponding to the light-emitting units 13 which are emitting light is collected; and in the next frame of picture, the light-emitting units 13 which emit light are shifted successively until all the light-emitting units 13 emit light via multiple frames of pictures. Apparently, the display panel reads fingerprint information via multiple frames of pictures. The smaller a quantity of light-emitting units 13 emitting light in each frame of picture, the larger a quantity of frames of pictures are required for reading of all fingerprint information and the longer time is required for the reading of all fingerprint information. For example, if a display panel reads fingerprint information using a picture scanning mode illustrated in FIG. 17A, i.e., the quantity of light-emitting units 13 emitting light simultaneously in each frame of picture (including 11×10 light-emitting units) is 9, then at least 12 frames of pictures need to be scanned for reading the fingerprint information of fingerprint recognition units 31 corresponding to all the light-emitting units 13. Time for reading fingerprint information is fixed for each frame of picture.

Figure 17B:
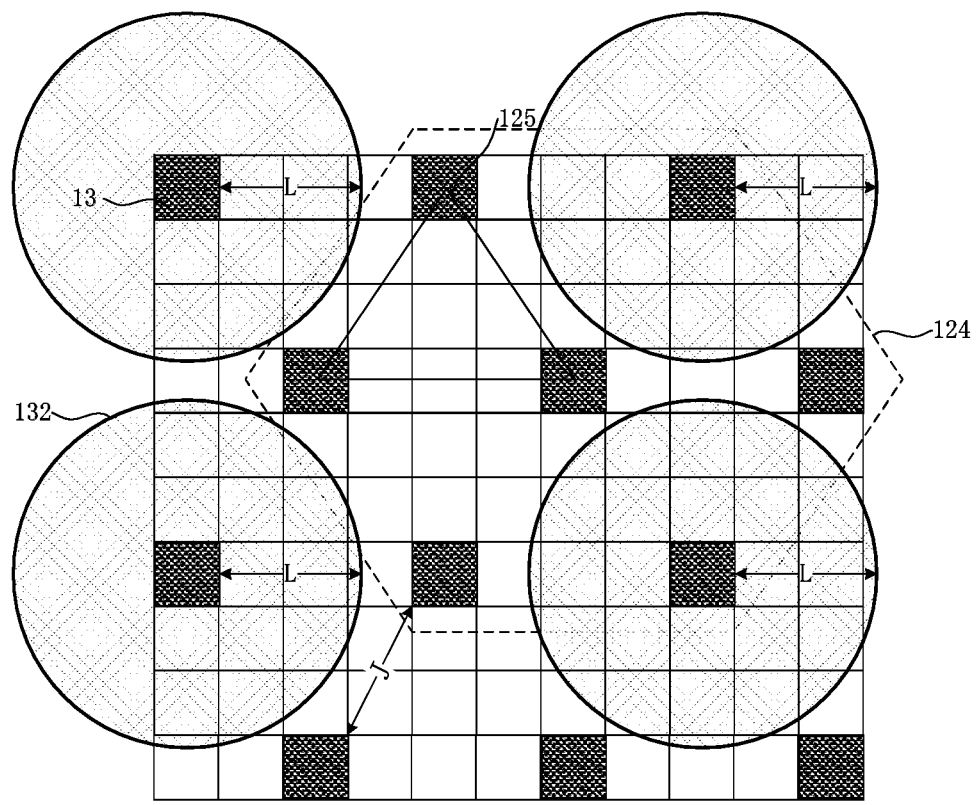

To reduce time required to read fingerprint information, optionally, multiple light-emitting units 13 in the first light-emitting dot array 124 illustrated in FIG. 17B form multiple patterns. Among the multiple patterns illustrated in FIG. 17B, each angle of a smallest pattern 125 is not equal to 90°. Apparently, compared with FIG. 17A, a distance J between two adjacent light-emitting units 13 which are emitting light in the first light-emitting dot array 124 decreases, so a quantity of light-emitting units 13 which are emitting light in each frame of picture is larger. Specifically, the quantity of light-emitting units 13 which are emitting light simultaneously in each frame of picture (including 11×10 light-emitting units) is 12, so the reading of fingerprint information of fingerprint recognition units 31 corresponding to all light-emitting units 13 can be completed simply when at most 10 frames of pictures are scanned. The multiple light-emitting units 13 in the first light-emitting dot array 124 form multiple patterns and each angle of the smallest pattern 125 among the multiple patterns is not equal to 90°, thereby increasing the quantity of light-emitting units 13 which are emitting light simultaneously while ensuring that no signal interference occurs and thus significantly reducing the time required to read fingerprint information.

Figure 18A:
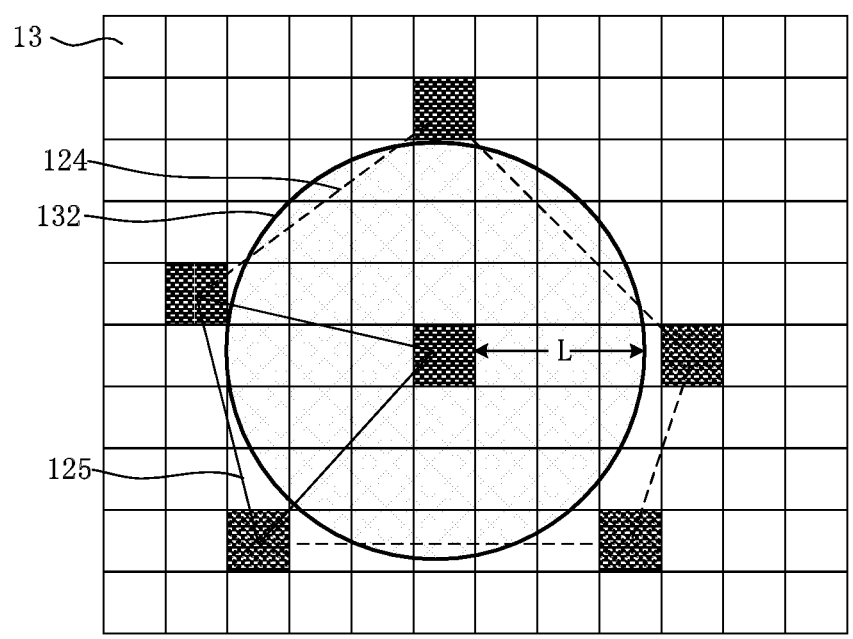
FIGS. 18A to 18C are schematic diagrams of three first light-emitting dot arrays according to embodiments of the present disclosure.

By way of example, based on the display panel described in any of the above embodiments, optionally, as illustrated in FIG. 18A, a first light-emitting dot array 124 may be a pentagonal light-emitting dot array including a central light-emitting unit 13 and five edge light-emitting units 13. The multiple light-emitting units 13 in the first light-emitting dot array 124 form multiple patterns and each angle of the smallest pattern 125 among the multiple patterns is not equal to 90°. The pentagonal light-emitting dot array can increase a quantity of light-emitting units 13 which are emitting light simultaneously while ensuring that no signal interference occurs and thus can reduce time required to read fingerprint information.

Figure 18B:
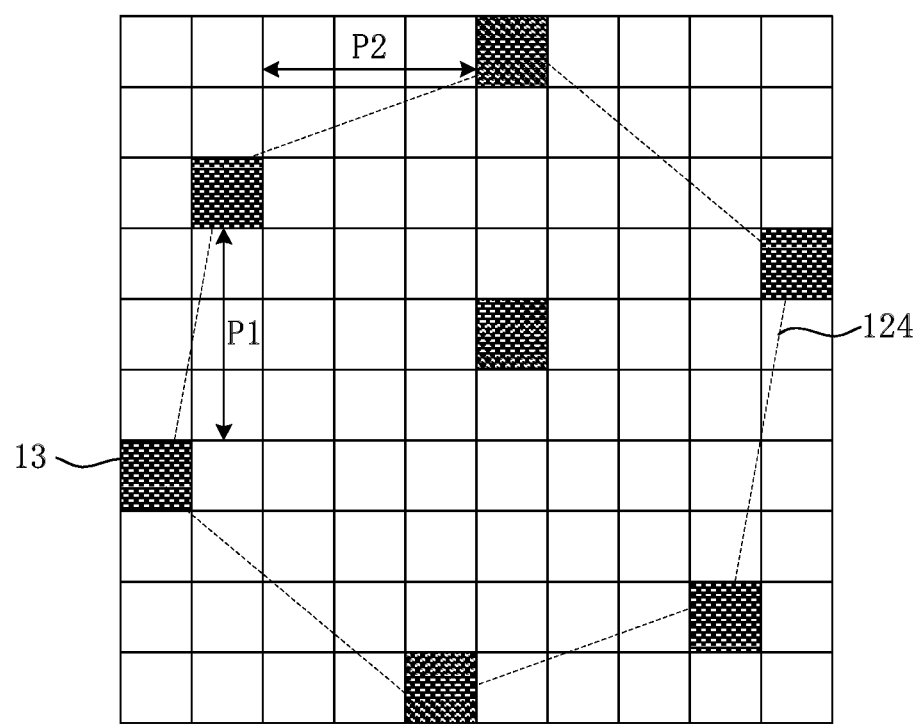

By way of example, based on the display panel described in any of the above embodiments, optionally, as illustrated in FIG. 18B, a first light-emitting dot array 124 may be a hexagonal light-emitting dot array including a central light-emitting unit 13 and six edge light-emitting units 13. The hexagonal light-emitting dot array can increase a quantity of light-emitting units 13 which emit light simultaneously while ensuring that no signal interference occurs and thus can reduce time required to read fingerprint information.

Figure 18C:
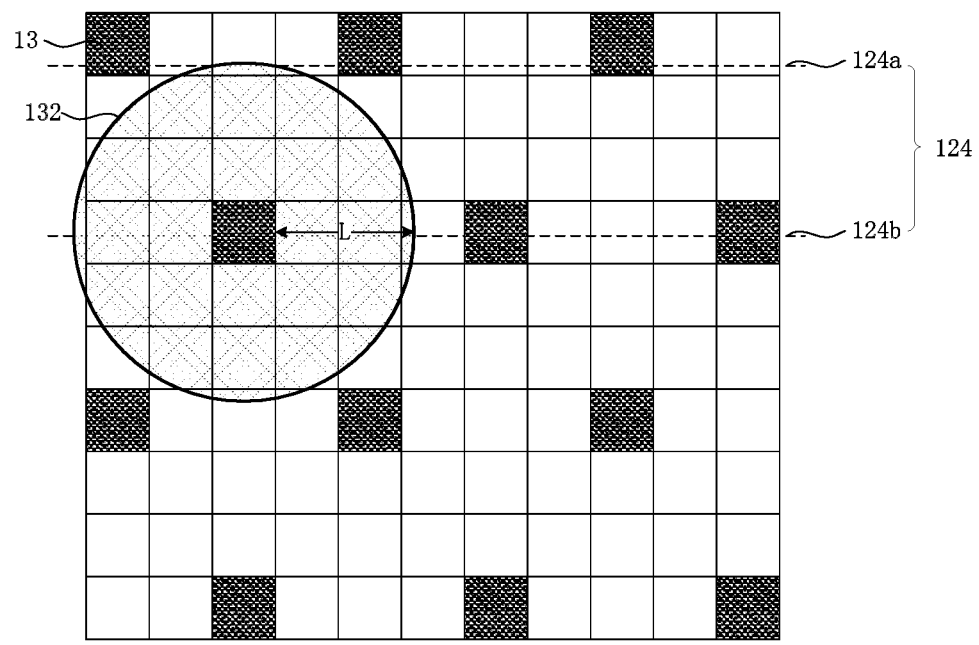

By way of example, based on the display panel described in any of the above embodiments, as illustrated in FIG. 18C, optionally, a first light-emitting dot matrix 124 may be composed of first light-emitting rows 124a and second light-emitting rows 124b which are alternately arranged. Any light-emitting unit 13 in the first light-emitting rows 124a and any light-emitting unit 13 in the second light-emitting rows 124b are disposed in different columns. Compared with the scanning mode of FIG. 17A, such configurations increase a quantity of light-emitting units 13 which emit light simultaneously while ensuring no signal interference occurs. The quantity of light-emitting units 13 which emit light simultaneously in each frame of picture (including 11×10 light-emitting units) is 12, so reading of fingerprint information of fingerprint recognition units 31 corresponding to all light-emitting units 13 can be completed simply when at most 10 frames of pictures are scanned, thereby significantly reducing time required to read fingerprint information.

For any first light-emitting dot array 124 in any of the above embodiments, optionally, the distance J between any two adjacent light-emitting units 13 in the first light-emitting dot array 124 is equal to the minimum non-interference distance L. Apparently, a respective fingerprint recognition unit 31 corresponding to each light-emitting unit 13 in the first light-emitting dot array 124 does not receive interference signals from other light-emitting units emitting light simultaneously, thus ensuring the fingerprint signal accuracy. Meanwhile, when the distance J between any two adjacent light-emitting units 13 in the first light-emitting dot matrix 124 is equal to the minimum non-interference distance L, the quantity of light-emitting units 13 which emit light simultaneously increases and the time required to read fingerprint signals decreases, i.e., the fingerprint reading efficiency increases.

Optionally, for any first light-emitting dot array 124 in any one of the above embodiments, for any two adjacent light-emitting units 13 in different rows in the first light-emitting dot array 124, a vertical distance P1 (as illustrated in FIG. 18B) between a row in which one light-emitting unit 13 is located and another row in which the other light-emitting unit 13 is located is less than the minimum non-interference distance L; and/or for any two adjacent light-emitting units 13 in different columns in the first light-emitting dot array 124, a horizontal distance P2 (as illustrated in FIG. 18B) between a column in which one light-emitting unit 13 is located and another column in which the other light-emitting unit 13 is located is less than the minimum non-interference distance L. The first light-emitting dot array 124 ensures that the respective fingerprint recognition unit 31 corresponding to each light-emitting unit 13 in the first light-emitting dot array 124 does not receive interference signals from other light-emitting units which emit light at the same time, thus improving the fingerprint recognition accuracy. Meanwhile, the quantity of light-emitting units 13 which emit light simultaneously increases and the time required to read fingerprint signals decreases, i.e., the fingerprint reading efficiency increases.

A square array scanning mode and a hexagonal array scanning mode are used as examples to clearly illustrate the fingerprint reading efficiency of the display panel provided by the embodiment of the present disclosure. Interference can be avoided when a distance between two adjacent light-emitting units 13 which are emitting light in each scanning picture is larger than or equal to a length of at least 20 light-emitting units 13 (a distance between two centers of two light-emitting units). Specifically, the length of 20 light-emitting units 13 is 20 P.

Figure 19A:
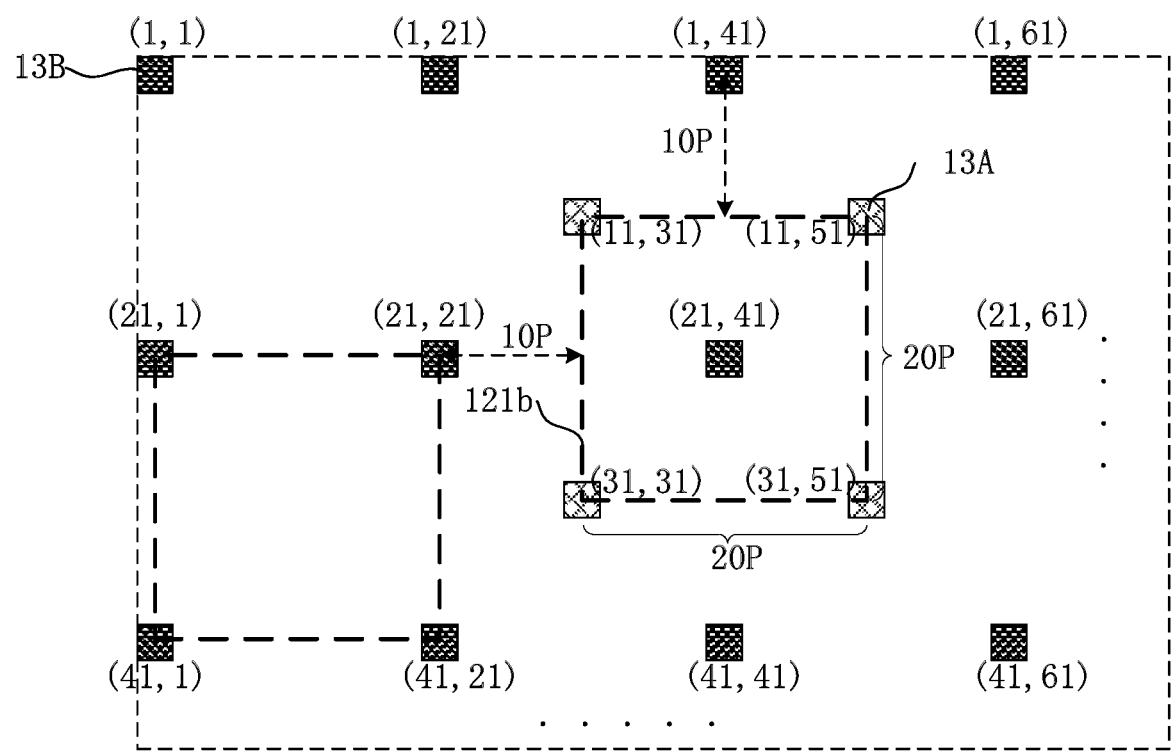
FIG. 19A is a schematic diagram illustrating a square array scanning mode of a display panel according to an embodiment of the present disclosure.

Referring to FIG. 19A, coordinates of each light-emitting unit 13 are (row, column). In a square array scanning mode of FIG. 19A, coordinates of light-emitting units 13B which emit light in a first row are (1, 1), (1, 21), (1, 41), . . . in sequence, coordinates of light-emitting units 13B which emit light in a second row are (21, 1), (21, 21), (21, 41), . . . in sequence, coordinates of light-emitting units 13B which emit light in a third row are (41, 1), (41, 21), (41, 41), . . . in sequence, and so on. A display panel is divided vertically and horizontally into multiple identical lightspot areas 121b with each light-emitting unit 13B which are emitting light (excluding the light-emitting units 13B at an edge of the display panel) as a center point. The lightspot areas 121b are equal in size. Each lightspot area 121b includes a light-emitting unit 13B which is emitting light and multiple light-emitting units 13A which are not emitting light around the light-emitting unit 13B which is emitting light.

By way of example, a lightspot area 121b corresponding to a light-emitting unit 13 (21, 41) which is emitting light is enclosed by four light-emitting units 13A (11, 31), (11, 51), (31, 31) and (31, 51) which are not emitting light. Apparently, a length and a width of this lightspot area 121b are both 20 P, i.e., a quantity of light-emitting units constituting this lightspot area 121b is 20×20=400. However, only one light-emitting unit 13B (21, 41) is emitting light in this lightspot area 121b, i.e., one light-emitting unit 13B is turned on among every 400 light-emitting units 13, so a density of light-emitting units 13B which are turned on in this lightspot area 121b is 1/400. All light-emitting units 13 in the display panel are divided into multiple lightspot areas 121b, so a density of light-emitting units 13B which emit light in each frame of picture is 1/400. Thus, to turn on all the light-emitting units 13 in the display panel, it needs to scan 20×20=400 frames of pictures. FIG. 19A illustrates only part of light-emitting units 13B which are emitting light simultaneously and their coordinates as well as light-emitting units 13A which are not emitting light at four vertexes of one lightspot area 121b and their coordinates.

Figure 19B:
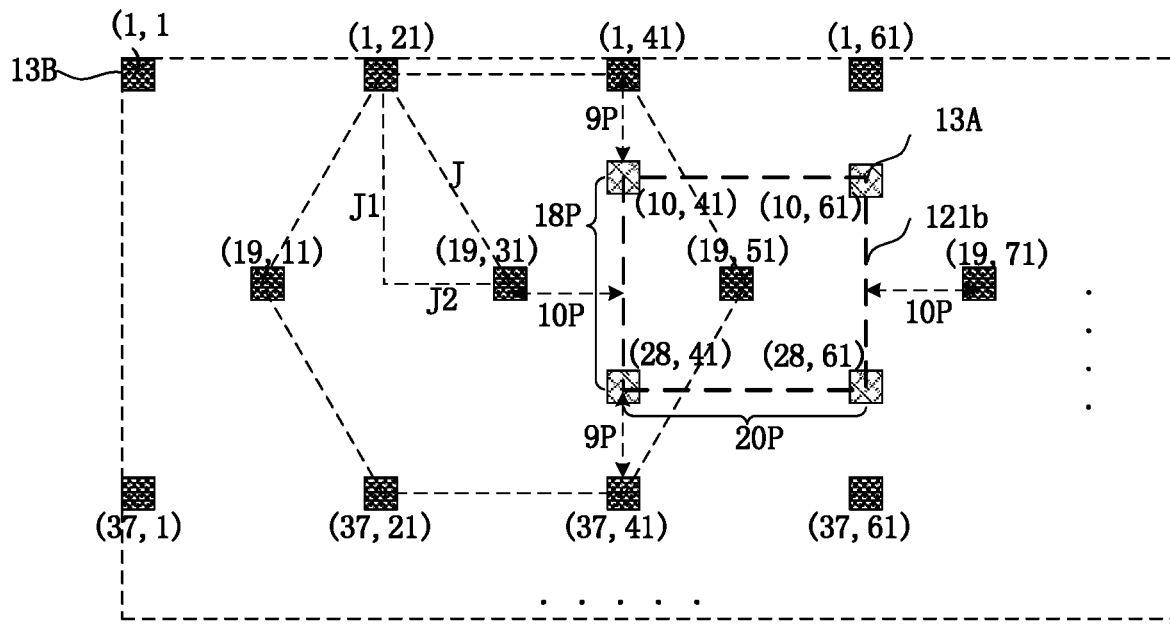
FIG. 19B is a schematic diagram illustrating a hexagonal array scanning mode of a display panel according to an embodiment of the present disclosure.

For a hexagonal array scanning mode of FIG. 19B, in the hexagonal array, a distance J between any two adjacent light-emitting units 13B which are emitting light reaches 20 light-emitting units 13B (20 P). A distance J1 between a row where a central light-emitting unit 13B is located and an edge light-emitting unit 13B in a row different from the row where the central light-emitting unit 13B is located is 10 P √3≈18 P. A distance J2 between a column where the central light-emitting unit 13B is located and an edge light-emitting unit 13B in a row different from the row where the central light-emitting unit 13B is located reaches 10 P. Thus, coordinates of light-emitting units 13B which are emitting light in the first row are (1, 1), (1, 21), (1, 41), . . . in sequence, coordinates of light-emitting units 13B which are emitting light in the second row are (19, 11), (19, 31), (19, 51), . . . in sequence, and coordinates of light-emitting units 13B which are emitting light in the third row are (37, 1), (37, 21), (37, 41), . . . in sequence, and so on. Apparently, when the light-emitting units 13B are turned on (emitting light), in a case where a distance between two adjacent light-emitting units 13B which are emitting light at a same row remains 20 P, a shortest distance between a first row where a first light-emitting unit 13B which is emitting light is located and a second row where a second light-emitting unit 13B which is emitting light at the same time is located decreases form 20 P to 18 P. In this case, a distance between the central light-emitting unit 13B and an edge light-emitting unit 13B in a row different from the row where the central light-emitting unit 13B is located is $\sqrt{(10P)^2+(18P)^2} \approx 20.59$ P>20 P, satisfying requirements of interference prevention.

All light-emitting units 13 of the display panel is divided into multiple identical lightspot areas 121b by dividing the display panel vertically and horizontally with each light-emitting unit 13B which is emitting light (excluding each light-emitting unit 13B at an edge of the display panel) as a center point. The lightspot areas 121b are equal in size. Each lightspot area 121b includes a light-emitting unit 13B which is emitting light and multiple light-emitting units 13A which are not emitting light around the light-emitting unit 13B which is emitting light.

By way of example, a lightspot area 121b corresponding to the light-emitting unit 13B (19, 51) which is emitting light is enclosed by four light-emitting units 13A (10, 41), (10, 61), (28, 41) and (28, 61) which are not emitting light.

Apparently, a length in a row direction of this lightspot area 121b is 20 P and a length in a column direction of this lightspot area is 18 P, i.e., a quantity of light-emitting units constituting this lightspot area 121b is 20×18=360.

However, only one light-emitting unit 13B (19, 51) is emitting light in this lightspot area 121b, i.e., one light-emitting unit 13B is turned on among every 360 light-emitting units 13, so a density of light-emitting units 13B which is emitting light in this lightspot area 121b is 1/360. The display panel is divided into lightspot areas 121b, so a density of light-emitting units 13B which emit light in each frame of picture is 1/360. Thus, the light-emitting units 13 in the display panel can all be turned on only after 20×18=360 frames of pictures have been scanned. FIG. 19B illustrates only part of light-emitting units 13B which are emitting light simultaneously and their coordinates as well as light-emitting units 13A which are not emitting light at four vertexes of one lightspot area 121b and their coordinates.

Apparently, the hexagonal array scanning mode illustrated in FIG. 19B is superior to the square array scanning mode illustrated in FIG. 19A.

Figure 20:
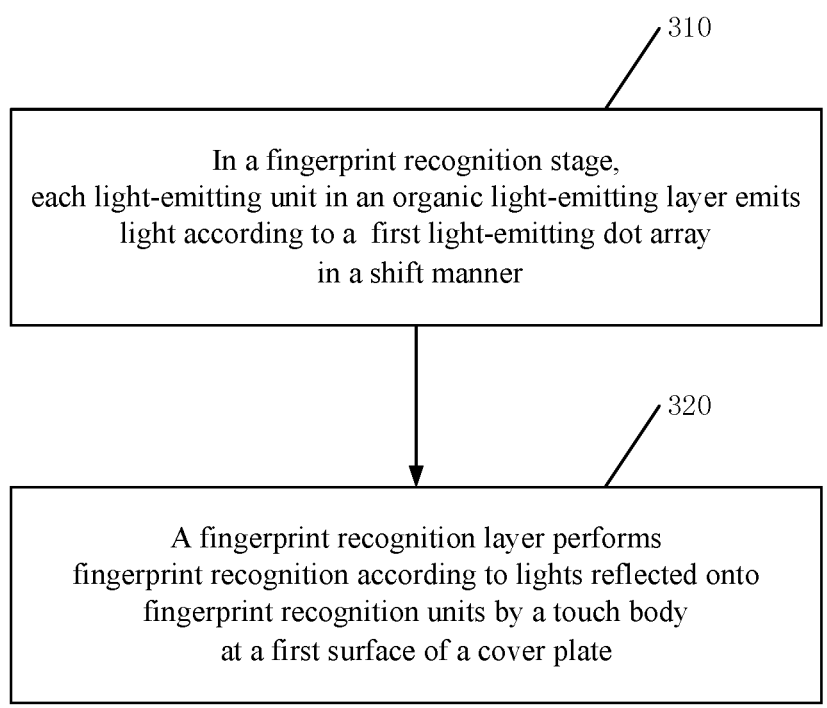
FIG. 20 is a flowchart illustrating a fingerprint recognition method of a display panel according to an embodiment of the present disclosure.

Additionally, an embodiment of the present disclosure provides a fingerprint recognition method for the display panel of FIGS. 15A to 15B. The display panel includes a display module 1 and a plurality of fingerprint recognition units 31. The display module 1 includes a substrate 10, and a plurality of light-emitting units 13 on a side of the substrate 10. The fingerprint recognition units 31 are on a light-emitting surface of the light-emitting units 13 facing away from the display panel. As illustrated in FIG. 20, the fingerprint recognition method of the present embodiment includes steps below.

In step 310, in a fingerprint recognition stage, the plurality of light-emitting units in an organic light-emitting layer emit light according to a first light-emitting dot array in a shift manner. A distance between any two adjacent light-emitting units in the first light-emitting dot array is greater than or equal to a minimum non-interference distance. The minimum non-interference distance refers to a maximum radius of a coverage area formed by lights emitted from any light-emitting unit and then reflected onto a fingerprint recognition layer by a touch body.

In step 320, the fingerprint recognition layer performs fingerprint recognition according to lights reflected onto the plurality of fingerprint recognition units by the touch body. In the present embodiment, the touch body may be a user's finger.

The display panel of the present embodiment performs the fingerprint recognition method using a picture scanning mode. When displaying one picture, the plurality of light-emitting units emit light according to the first light-emitting dot array in a shift manner. The distance between any two adjacent light-emitting units in the first light-emitting dot array is greater than or equal to the minimum non-interference distance, so the fingerprint signal lights formed by lights emitted from a respective light-emitting unit and then reflected by the fingerprint of the user's finger is not incident onto fingerprint recognition units corresponding to other light-emitting units in the dot array. Therefore, a fingerprint recognition unit corresponding to a corresponding light-emitting unit in the first light-emitting dot array receives only fingerprint signal light formed by the light emitted from the corresponding light-emitting unit. That is, each fingerprint recognition unit does not receive interference signals from other light-emitting units. Accordingly, an inductive signal produced by each fingerprint recognition unit accurately represents reflection of light emitted from a corresponding light-emitting unit on the fingerprint of the user's finger. Therefore, the display panel of the present embodiment improves fingerprint recognition accuracy.

When located on the side of the light-emitting units 13 facing away from the substrate 10, the fingerprint recognition units 31 (including the first fingerprint recognition units 311 and the second fingerprint recognition units 312) are likely to affect the light-emitting angles of the light-emitting units 13. Therefore, solutions are provided below to improve a display effect of the display panel.

Figure 21:
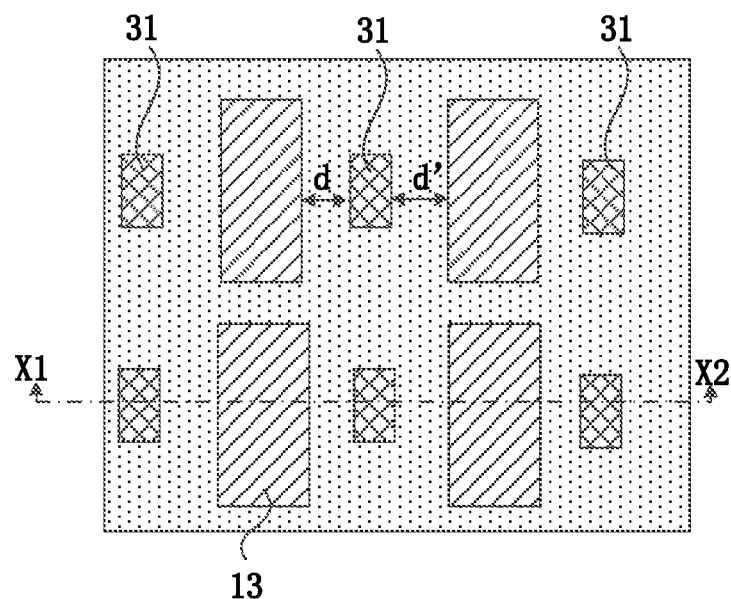
FIG. 21 is a schematic diagram of another display panel according to an embodiment of the present disclosure.
Figure 22:
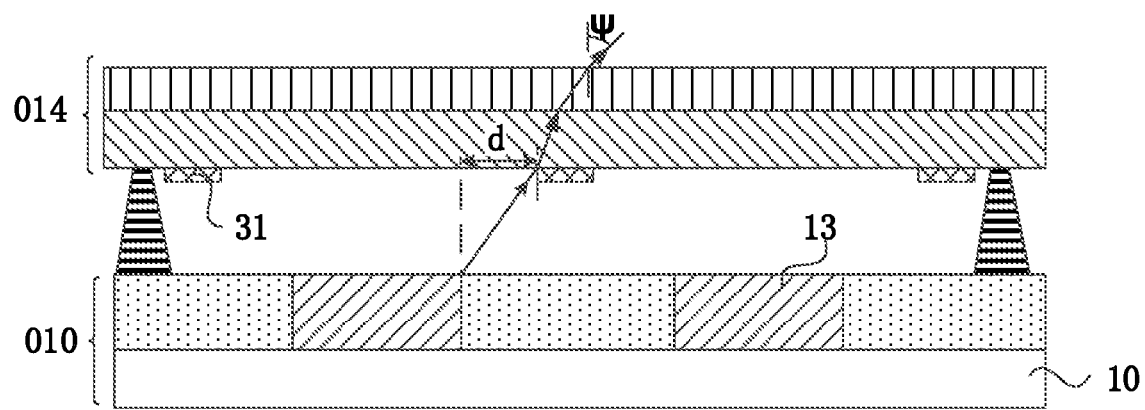
FIG. 22 is a cross sectional view of the display panel in FIG. 21 taken along a cut line X1-X2.

FIG. 21 is a structural diagram of another display panel according to an embodiment of the present disclosure. FIG. 22 is a cross sectional view of the display panel of FIG. 21 taken along a section line X1-X2. Referring to FIGS. 21 and 22, the display panel includes an array substrate 010, an encapsulation layer 014 and at least one fingerprint recognition unit 31 on the encapsulation layer 014.

The array substrate 010 includes a substrate 10 and a plurality of light-emitting units 13 on the substrate 10.

The encapsulation layer 014 is provided on a side of the plurality of light-emitting units 13 facing away from the substrate 10. At least one fingerprint recognition unit 31 is provided on the encapsulation layer 014. A vertical projection of the at least one fingerprint recognition unit 31 onto the substrate 010 is in a non-light-emitting area of the array substrate 010. The non-light-emitting area is between adjacent light-emitting units 13.

A horizontal distance d between an edge of the fingerprint recognition unit 31 and an edge of a closest light-emitting unit 13 is greater than or equal to a preset distance so that the display panel reaches a maximum light-emitting angle $\psi$, where $\psi$ is greater than or equal to 50°.

Specifically, referring to FIG. 22, the maximum light-emitting angle $\psi$ of the display panel refers to a maximum included angle between the light emitted from the light-emitting surface of the display panel and a perpendicular of the light-emitting surface of the display panel. The greater the maximum light-emitting angle ψ of the display panel, the greater a viewing angle of the display panel.

Among the light-emitting units 13 adjacent to the fingerprint recognition unit 31, the light-emitting unit 13 having an edge closest to the edge of the fingerprint recognition unit 31 is the closest light-emitting unit 13 of the fingerprint recognition unit 31.

Figure 23:
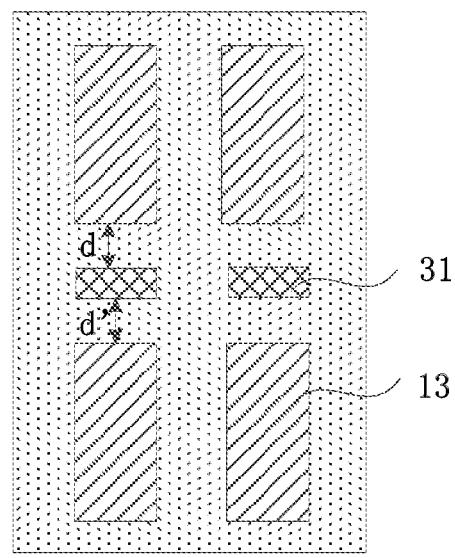
FIG. 23 is a structural diagram of another display panel according to an embodiment of the present disclosure.

FIG. 23 is a structural diagram of another display panel according to an embodiment of the present disclosure. Referring to FIGS. 21 and 23, the non-light-emitting area may be an area between two adjacent columns of light-emitting units 13 or an area between two adjacent rows of light-emitting units 13 depending on an arrangement of the light-emitting units 13 in the display panel. The configuration of the non-light-emitting area is not limited. Referring to FIGS. 21 and 23, the closest light-emitting unit 13 of the fingerprint recognition unit 31 may be determined based on a distance d from one of the two columns (rows) of light-emitting units 13 adjacent to the fingerprint recognition unit 31 to the edge of the fingerprint recognition unit 31 and a distance d' from the other one of the two columns (rows) of light-emitting units 13 adjacent to the fingerprint recognition unit 31 to the edge of the fingerprint recognition unit 31. The light-emitting unit 13 with a shorter distance to the fingerprint recognition unit 31 is the closest light-emitting unit 13 of the fingerprint recognition unit 31.

Additionally, in the present embodiment, ψ is set to a value greater than or equal to 50° to satisfy a user's basic requirements for the viewing angle of the display panel so that the user can view a clear display picture when viewing the picture in a lateral direction. ψ may also be set to a value greater than or equal to 60°, 70°, etc. according to a user's basic requirements for the viewing angle of the display panel. The value of ψ is not limited.

In the present embodiment, the fingerprint recognition unit 31 is disposed on the encapsulation layer 014 of the display panel and the vertical projection of the fingerprint recognition unit 31 onto the array substrate 010 is located in the non-light-emitting area of the array substrate 010, so that the fingerprint recognition unit 31 can be disposed in the display area of the display panel, thereby increasing a screen-to-body ratio of the display panel and following a trend towards a narrow bezel of a display panel. Since a lower surface of the fingerprint recognition unit 31 is light-proof, when the light emitted from the light-emitting unit 13 is incident onto the edge of the fingerprint recognition unit 31, this light is blocked by the lower surface of the fingerprint recognition unit 31, thus affecting the light-emitting angle of the display panel. In the present embodiment, the horizontal distance d between the edge of the fingerprint recognition unit 31 and the light-emitting area edge of the closest light-emitting unit 13 is set to a value greater than or equal to the preset distance, so that the fingerprint recognition unit 31 disposed in the display area of the display panel does not affect the light-emitting angle of the display panel, thereby ensuring that the display panel has a large viewing angle.

Figure 24:
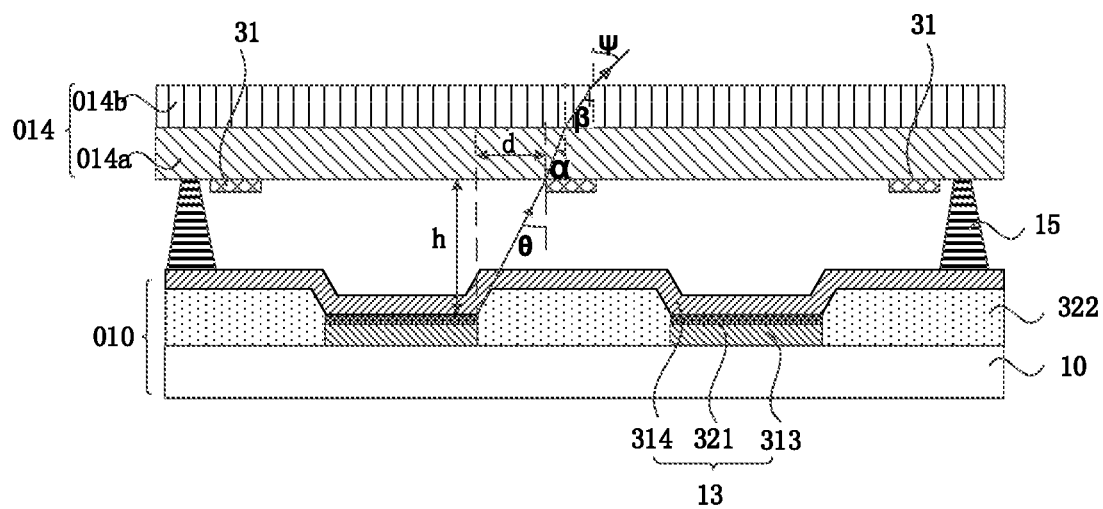
FIG. 24 is a cross sectional view of another display panel according to an embodiment of the present disclosure.

FIG. 24 is a cross sectional view of another display panel according to an embodiment of the present disclosure. Optionally, referring to FIG. 24, the light-emitting unit 13 includes an anode 314, a light-emitting function layer 321 and a cathode 313. The light-emitting function layer 321 is disposed between the anode 314 and the cathode 313. An array substrate 010 further includes a pixel-defining layer 322. The pixel-defining layer 322 has opening areas. The light-emitting function layer 321 of each light-emitting unit 13 is located in a respective opening area.

The cathode 314 covers the light-emitting function layer 321 and a non-opening area of the pixel-defining layer 322.

A vertical projection of a fingerprint recognition unit 31 onto the array substrate 010 is located in the non-opening area of the pixel-defining layer 322.

Specifically, the light-emitting function layer 321 may be a red light-emitting layer, a green light-emitting layer or a blue light-emitting layer. Since a substrate 10 is further provided with a driver circuit (not illustrated in FIG. 24) for driving the light-emitting units 13, the pixel-defining layer 322 is used for, on the one hand, covering the driver circuit and other structures to make the substrate 10 flat and, on the other hand, defining light-emitting areas and non-light-emitting areas on the array substrate 010, i.e., defining each light-emitting unit 13. The opening areas of the pixel-defining layer 322 are the light-emitting areas of the array substrate 010 and the non-opening areas of the pixel-defining layer 322 are the non-light-emitting areas of the array substrate 010.

Optionally, referring to FIG. 24, an encapsulation layer 014 includes a transparent rigid cover plate 014a and a film 014b. The fingerprint recognition unit 31 is disposed on a side of the transparent rigid cover plate 014a facing the array substrate 010.

So d≥h*tan ψ applies, where h denotes a vertical distance from the fingerprint recognition unit 31 to a light-emitting side of the light-emitting function layer 321 of the light-emitting unit 13.

Specifically, referring to FIG. 24, a support 15 is disposed between the transparent rigid cover plate 014a and the array substrate 010 to support the transparent rigid cover plate 014a, and a gap between the transparent rigid cover plate 014a and the array substrate 010 is filled with air or nitrogen. Light emitted from the light-emitting function layer 321 of the light-emitting unit 13 is transmitted to air after passing through the cathode 314, the gap between the transparent rigid cover plate 014a and the array substrate 010, and the encapsulation layer 014. Since a thickness of the cathode 314 is thin and has little impact on light propagation, light refraction by the cathode 314 is negligible during light propagation. According to the refraction law, the following formula can be obtained:

$$n_1 \sin \theta = n_2 \sin \alpha = n_3 \sin \beta = n_1 \sin \psi.$$

From the above formula, the following formulas can be obtained: $\theta = \psi$ and $$\tan \psi = \tan \theta = \frac{d}{h}.$$

Thus, when the display panel reaches the maximum light-emitting angle ψ, a formula d=h*tan ψ applies. Therefore, a preset distance is h*tan ψ, and when d is greater than or equal to h*tan ψ, the display panel reaches the maximum light-emitting angle ψ.

$n_1$ refers to a refractive index of the air, $n_2$ refers to a refractive index of the transparent rigid cover plate 014a, and $n_3$ refers to a refractive index of the film 014b. θ refers to a propagation angle of the light in the gap between the transparent rigid cover plate 014a and the array substrate 010, α refers to a propagation angle of light in the transparent rigid cover plate 014a, and β refers to a propagation angle of light in the film 014b. The propagation angle refers to an angle between the light and a perpendicular of each film of the display panel.

Optionally, if h=4 µm and ψ≥50°, then d≥4.8 µm. h may be calculated according to the thickness of the cathode 314, a thickness of the pixel-defining layer 322 and a thickness of the support 15. It should be noted that h=4 µm is obtained according to an industry-wide thickness of each film of the display panel. When the thickness of each film of the display panel is changed, h may take other values. The value of h is not limited in the present disclosure.

In the present embodiment, the fingerprint recognition unit 31 is disposed on the side of the transparent rigid cover plate 014a facing the array substrate 010, and the horizontal distance d between the edge of the fingerprint recognition unit 31 and the light-emitting area edge of the closest light-emitting unit 13 is set to a value greater than or equal to h*tan ψ. Therefore, the fingerprint recognition unit 31 can be disposed in the display area of the display panel, thereby increasing the screen-to-body ratio of the display panel. Further, the display panel can reach the maximum light-emitting angle ψ, thereby ensuring that the display panel has a large viewing angle and thus improving user experience. Furthermore, in the manufacturing process of the display panel, the fingerprint recognition unit 31 may be first formed on a surface of the transparent rigid cover plate 014a, and then the transparent rigid cover plate 014a may be bonded to the array substrate 010, so that a high-temperature process or the like in a manufacturing process of the fingerprint recognition unit 31 does not affect the light-emitting unit 13 and other structures on the array substrate 010.

Figure 25:
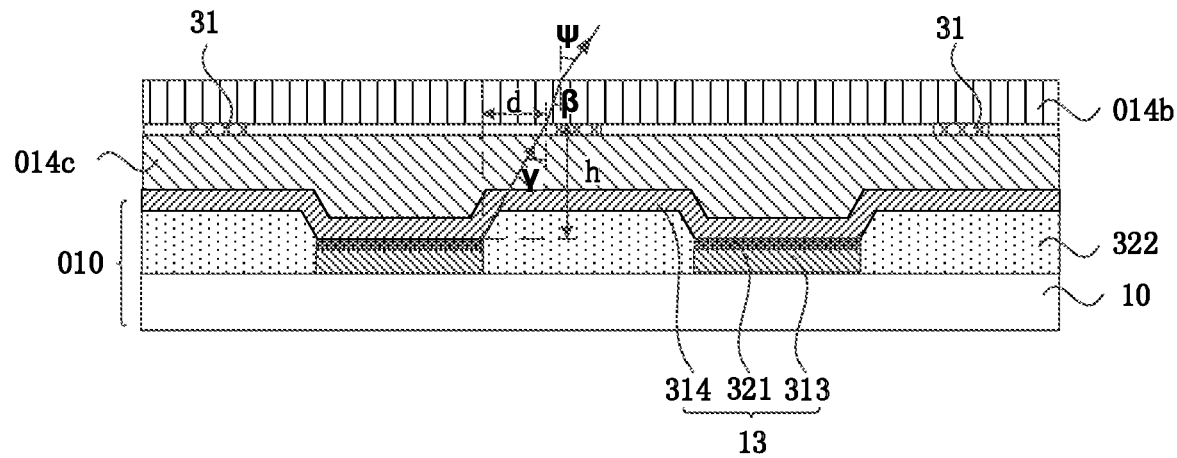
FIG. 25 is a cross sectional view of another display panel according to an embodiment of the present disclosure.

FIG. 25 is a cross sectional view of another display panel according to an embodiment of the present disclosure. Optionally, referring to FIG. 25, the encapsulation layer 014 includes a thin film encapsulation layer 014c, and the fingerprint recognition units 31 are disposed on a side of the thin film encapsulation layer 014c facing away from the array substrate 010. Specifically, the thin film encapsulation layer 014c may include organic layers and inorganic layers which are alternately arranged, and the inorganic layers are disposed on both sides of the thin film encapsulation layer 014c so as to better resist water and oxygen.

Specifically, if a processing temperature of the fingerprint recognition unit 31 is low, other films of the display panel are not affected in the manufacturing process and the fingerprint recognition unit 31 may be formed directly on the surface of the thin film encapsulation layer 014c. If the processing temperature of the fingerprint recognition unit 31 is high, the light-emitting unit 13 may be affected in the manufacturing process, then the fingerprint recognition unit 31 may be first formed on a substrate and then the substrate may be bonded to the thin film encapsulation layer 014c.

Optionally, referring to FIG. 25, the fingerprint recognition unit 31 is formed on the surface of the thin film encapsulation layer 014c facing away from the array substrate 010.

Then $$\frac{n_{TFE} * d}{\sqrt{d^2 + h^2}} \geq \sin\psi$$

applies, where h denotes a vertical distance from the fingerprint recognition unit 31 to a light-emitting side of a light-emitting function layer 321 of the light-emitting unit 13 and $n_{TFE}$ denotes a refractive index of the thin film encapsulation layer 014c.

Specifically, referring to FIG. 25, the lights emitted from the light-emitting function layer 321 of the light-emitting unit 13 are transmitted to air after passing through the cathode 314, the thin film encapsulation layer 014c and the film 014b. Since a thickness of the cathode 314 is thin and has little impact on light propagation, light refraction by the cathode 314 is negligible during light propagation. A thickness of the fingerprint recognition unit 31 is thin and negligible. According to the refraction law, the following formulas can be obtained:

$$n_{TFE}\sin\gamma = n_3\sin\beta = n_1\sin\psi \text{ and}$$

$$\sin\gamma = \frac{d}{\sqrt{d^2 + h^2}}.$$

From the above formulas, the following formula can be obtained:

$$\frac{n_{TFE} * d}{\sqrt{d^2 + h^2}} = \sin\psi.$$

Thus, when the display panel reaches a maximum light-emitting angle ψ, a formula $$\frac{n_{TFE} * d}{\sqrt{d^2 + h^2}} = \sin\psi$$

applies. Therefore, when $$\frac{n_{TFE} * d}{\sqrt{d^2 + h^2}} \geq \sin\psi$$

applies, the display panel reaches the maximum light-emitting angle ψ.

$n_1=1$ and $n_3$ denotes a refractive index of the film 014b. γ denotes a propagation angle of light in the thin film encapsulation layer 014c, and β denotes a propagation angle of light in another film 014b.

Optionally, if h=8 µm, $n_{TFE}$=1.5 and ψ≥50°, then d≥4.7 µm applies. h may be calculated according to the thickness of the thin film encapsulation layer 014c and the thickness of the cathode 314. Furthermore, since thick material is typically organic material and inorganic material is light and thin in the thin film encapsulation layer 014c, the refractive index of the thin film encapsulation layer 014c may be the refractive index of the organic material, i.e., 1.5. The value of h is obtained according to an industry-wide thickness of each film of the display panel. When the thickness of each film of the display panel is changed, h may take other values. The value of h is not limited in the present disclosure.

Figure 26:
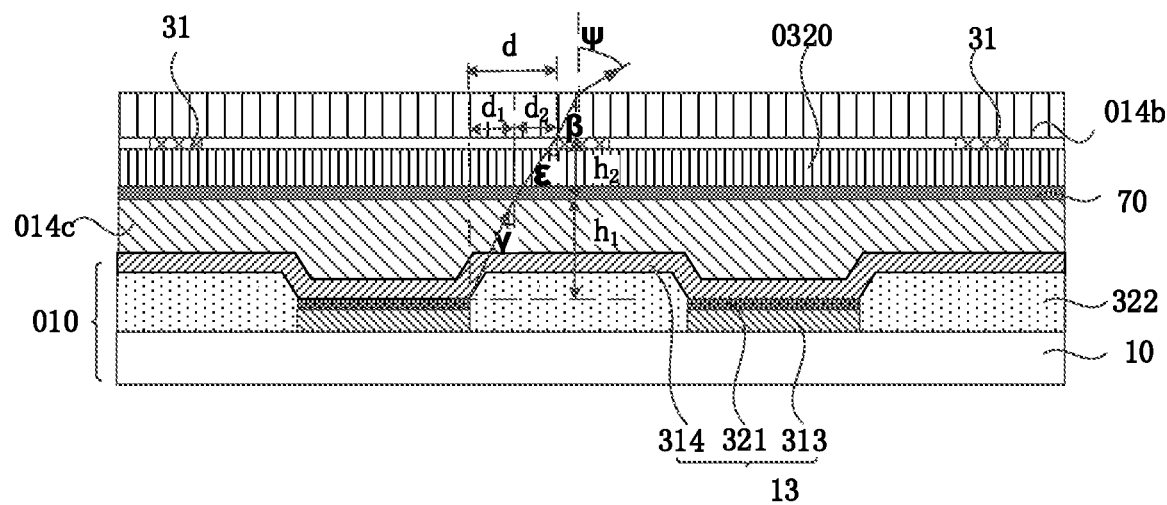
FIG. 26 is a cross sectional view of another display panel according to an embodiment of the present disclosure.

FIG. 26 is a cross sectional view of another display panel according to an embodiment of the present disclosure. Referring to FIG. 26, the fingerprint recognition unit 31 further includes a third substrate 0320. The fingerprint recognition unit 31 is formed on the third substrate 0320, and a side of the third substrate 0320 facing away from the fingerprint recognition unit 31 is bonded by an adhesive layer 70 to the surface of the thin film encapsulation layer 014c facing away from the array substrate 010.

Then $d=d_1+d_2$, where $$\frac{n_{TFE}*d_1}{\sqrt{d_1^2+h_1^2}} \geq \sin\psi \text{ and } \frac{n_{PI}*d_2}{\sqrt{d_2^2+h_2^2}} \geq \sin\psi$$

apply. $n_{TFE}$ denotes a refractive index of the thin film encapsulation layer 014c. $h_1$ denotes a vertical distance from an interface between the thin film encapsulation layer 014c and the adhesive layer 70 to the light-emitting side of the light-emitting function layer 321 of the light-emitting unit 13, and $d_1$ denotes a horizontal distance to an edge of the light-emitting unit 13 from an emitting point of light emitted from the edge of the light-emitting unit 13 on the interface between the thin film encapsulation layer 014c and the adhesive layer 70. $n_{PI}$ denotes a refractive index of the third substrate 0320. $h_2$ denotes a sum of the thickness of the adhesive layer 70 and the thickness of the third substrate 0320, and $d_2$ denotes a horizontal distance to an edge of the fingerprint recognition unit 31 from the emitting point of the light emitted from the edge of the light-emitting unit 13 on the interface between the thin film encapsulation layer 014c and the adhesive layer 70.

Specifically, referring to FIG. 26, the lights emitted from the light-emitting function layer 321 of the light-emitting unit 13 are transmitted to air after passing through a cathode 314, the thin film encapsulation layer 014c, the adhesive layer 70, the third substrate 0320 and the film 014b. Since the thickness of the cathode 314 and the thickness of the adhesive layer 70 are thin and have little impact on light propagation, light refractions by the cathode 314 and the adhesive layer 70 are ignored during light propagation. The thickness of the fingerprint recognition unit 31 is thin and negligible. According to the refraction law, the following formulas can be obtained:

$$n_{TFE}\sin\gamma = n_{PI}\sin\varepsilon = n_3\sin\beta = n_1\sin\psi,$$

$$\sin\gamma = \frac{d_1}{\sqrt{d_1^2+h_1^2}} \text{ and } \sin\varepsilon = \frac{d_2}{\sqrt{d_2^2+h_2^2}}.$$

From the above formulas, the following formulas can be obtained:

$$\frac{n_{TFE}*d_1}{\sqrt{d_1^2+h_1^2}} = \sin\psi \text{ and } \frac{n_{PI}d_2}{\sqrt{d_2^2+h_2^2}} = \sin\psi.$$

Thus, when the display panel reaches the maximum light-emitting angle $\psi$, the formulas $$\frac{n_{TFE}*d_1}{\sqrt{d_1^2+h_1^2}} = \sin\psi \text{ and } \frac{n_{PI}*d_2}{\sqrt{d_2^2+h_2^2}} = \sin\psi$$

apply. Therefore, when $$\frac{n_{TFE}*d_1}{\sqrt{d_1^2+h_1^2}} \geq \sin\psi \text{ and } \frac{n_{PI}*d_2}{\sqrt{d_2^2+h_2^2}} \geq \sin\psi$$

apply, the display panel reaches the maximum light-emitting angle $\psi$.

$n_1=1$ and $n_3$ denotes a refractive index of the film 014b. $\gamma$ denotes a propagation angle of light in the thin film encapsulation layer 014c, $\varepsilon$ denotes a propagation angle of light in the third substrate 0320, and $\beta$ denotes a propagation angle of light in another film 014b.

Optionally, if $h_1=8$ μm, $n_{TFE}=1.5$, $h_2=10$ μm, $n_{PI}=1.6$ and $\psi \geq 50°$, then $d_1 \geq 4.7$ μm and $d_2 \geq 5.4$ μm apply, and thus $d \geq 10.1$ μm applies.

In the present embodiment, the fingerprint recognition unit 31 is disposed on the side of the thin film encapsulation layer 014c facing away from the array substrate 010, and the horizontal distance d between the edge of the fingerprint recognition unit 31 and the light-emitting area edge of the closest light-emitting unit 13 is set to a value greater than or equal to a preset distance. As a result, the fingerprint recognition 31 can be disposed in the display area of the display panel, thereby increasing the screen-to-body ratio of the display panel. Further, the display panel can reach the maximum light-emitting angle $\psi$, thereby ensuring that the display panel has a large viewing angle and thus improving user experience. The fingerprint recognition unit 31 is provided after the thin film encapsulation layer 014c has been manufactured, ensuring that the thin film encapsulation layer 014c can block water and oxygen effectively and reducing a probability that the display panel is corroded.

Figure 27:
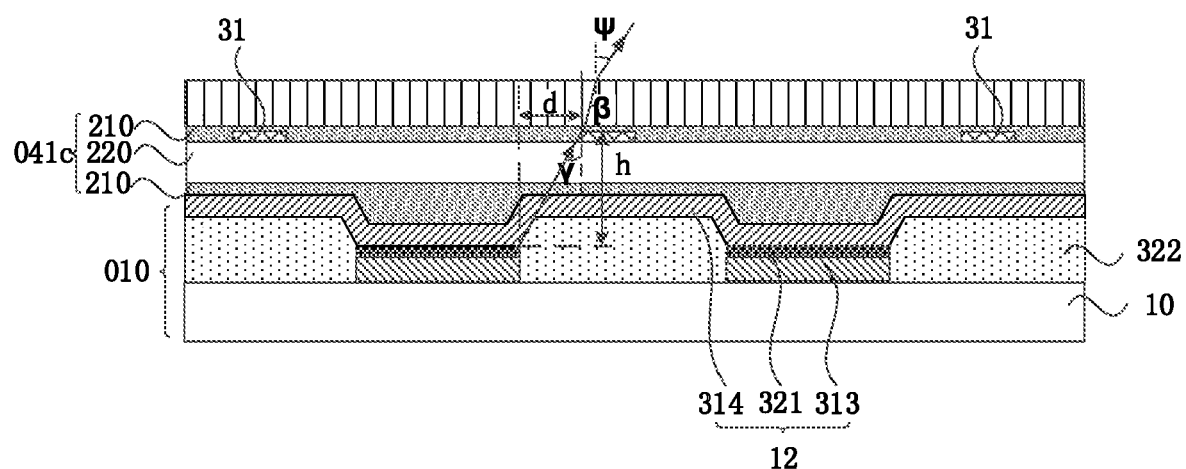
FIG. 27 is a cross sectional view of another display panel according to an embodiment of the present disclosure.

FIG. 27 is a cross sectional view of another display panel according to an embodiment of the present disclosure. Optionally, referring to FIG. 27, the fingerprint recognition unit 31 may also be disposed inside the thin film encapsulation layer 014c. The thin film encapsulation layer 014c may include inorganic layers 210 and organic layers 220 which are alternately arranged. The fingerprint recognition unit 31 may be disposed on a side of one organic layer 220 or one inorganic layer 210 facing away from the array substrate 010.

Referring to FIG. 27, the thin film encapsulation layer 014c includes two inorganic layers 210 and one organic layer 220, and the fingerprint recognition unit 31 is disposed directly on a surface of the organic layer 220 of the thin film encapsulation layer 014c facing away from the array substrate 010.

Since thicknesses of the inorganic layers 210 are thin and have little impact on light propagation, light refractions by the inorganic layers 210 are negligible. According to the refraction law, when the display panel reaches the maximum light-emitting angle $\psi$, a formula $$\frac{n_{TFE}*d}{\sqrt{d^2+h^2}} = \sin\psi$$

applies. Therefore, when $$\frac{n_{TFE}*d}{\sqrt{d^2+h^2}} \geq \sin\psi$$

applies, the display panel reaches the maximum light-emitting angle $\psi$.

Specifically, the fingerprint recognition unit 31 is disposed inside the thin film encapsulation layer 014c so that a vertical distance h from the fingerprint recognition unit 31 to a light-emitting side of a light-emitting function layer 321 of the light-emitting unit 13 is reduced and thereby a value range of d is larger, i.e., a position of the fingerprint recognition unit 31 can be configured more flexibly.

Moreover, the fingerprint recognition unit 31 may be disposed on the side of the thin film encapsulation layer 014c facing the array substrate 010 as long as the fingerprint recognition unit 31 is insulated from a cathode 314. When the fingerprint recognition unit 31 is disposed on the side of the thin film encapsulation layer 014c facing the array substrate 010, the vertical distance h from the fingerprint recognition unit 31 to the light-emitting side of the light-emitting function layer 321 is small and has little impact on the light-emitting angle of light emitted from the light-emitting function layer 321, so the preset distance may be any value greater than or equal to zero.

It should be noted that the film 014b in the above-described solutions may be a polarizer or a film such as a protective glass film disposed outside the display panel in a display device.

Figure 28:
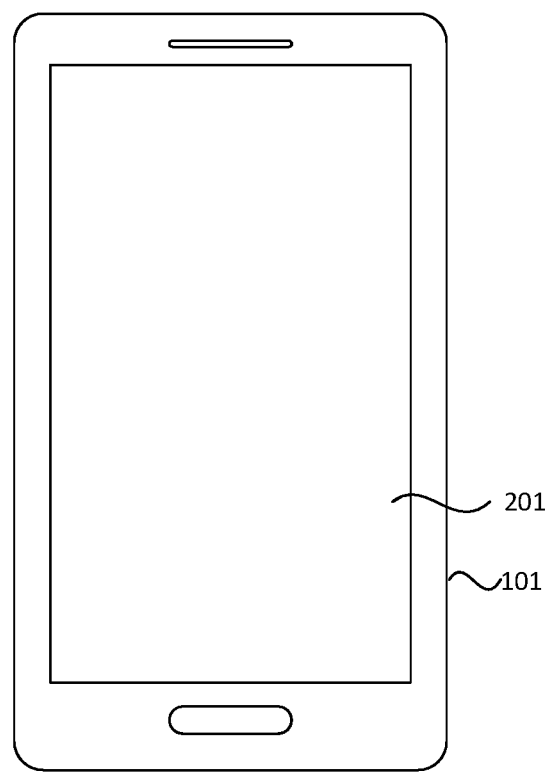
FIG. 28 is a schematic structural diagram of a display device according to an embodiment of the present disclosure.

Another embodiment of the present disclosure provides a display device. FIG. 28 is a structural diagram of the display device according to an embodiment of the present disclosure. Referring to FIG. 28, the display device 101 includes the display panel 201 of any embodiment of the present disclosure. The display device 101 may be a mobile phone, a tablet PC, an intelligent wearable device, etc.

In the display device provided by embodiments of the present disclosure, the first fingerprint recognition units and the second fingerprint recognition units are disposed in the display area of the substrate. This solves the problem of low screen-to-body ratio in an existing display panel, achieves the purpose of improving the low screen-to-body ratio of the display panel and meets the trend towards a narrow bezel of the display panel. Moreover, in embodiments of the present disclosure, the first fingerprint recognition unit and the second fingerprint recognition unit have different configuration parameters so as to detect the same electric signal value with respect to the same reflector. This achieves the purpose of improving the fingerprint recognition accuracy.

It is to be noted that the above are only part embodiments of the present disclosure and the technical principles used therein. It will be understood by those skilled in the art that the present disclosure is not limited to the embodiments described herein. Those skilled in the art can make various modifications, adaptations, combinations and substitutions without departing from the scope of the present disclosure. Therefore, although the present disclosure has been described in detail via the above embodiments, the present disclosure is not limited to the above embodiments and may include more other equivalent embodiments without departing from the concept of the present disclosure. The scope of the present disclosure is determined by the scope of the appended claims.

What is claimed is:

1. An array substrate, comprising:
   a substrate comprising a display area with a non-display area surrounding the display area;
   a plurality of light-emitting units located in the display area of the substrate, wherein the plurality of light-emitting units comprise a plurality of first light-emitting units configured to emit first color light, a plurality of second light-emitting units configured to emit second color light, and a plurality of third light-emitting units configured to emit third color light, wherein a light transmittance of the first color light and that of the second color light are both greater than that of the third color light; and
   a plurality of first fingerprint recognition units and a plurality of second fingerprint recognition units, which are located in the display area of the substrate, wherein
   a projection of each of the plurality of first fingerprint recognition units onto the substrate overlaps at least in part with a projection of an area between a respective one of the plurality of third light-emitting units and one of a respective one of the plurality of first light-emitting units and a respective one of the plurality of second light-emitting units onto the substrate;
   a projection of each of the plurality of second fingerprint recognition units onto the substrate does not overlap with the projection of the area between the third light-emitting unit and one of the first light-emitting unit and the second light-emitting unit onto the substrate; and
   the projection of each of the plurality of second fingerprint recognition units onto the substrate overlaps at least in part with a projection of an area between the respective one of the plurality of first light-emitting units and the respective one of the plurality of second light-emitting units onto the substrate; wherein the plurality of light-emitting units are configured to: in a fingerprint recognition stage, serve as light sources for the plurality of first fingerprint recognition units and the plurality of second fingerprint recognition units, and the plurality of first fingerprint recognition units and the plurality of second fingerprint recognition units have different configuration parameters for detecting an electric signal value with respect to a reflector.

2. The array substrate of claim 1, wherein
   each of the plurality of first fingerprint recognition units comprises a first photosurface located on a surface of each of the plurality of first fingerprint recognition units facing a display side; and
   each of the plurality of second fingerprint recognition units comprises a second photosurface located on a surface of each of the plurality of second fingerprint recognition units facing the display side; wherein
   an area of the first photosurface is greater than that of the second photosurface.

3. The array substrate of claim 2, wherein
   the plurality of light-emitting units are arranged in an array;
   the first photosurface comprises a first portion and a second portion; a projection of the first portion onto the substrate is within the projection of the area between the third light-emitting unit and one of the first light-emitting unit and the second light-emitting unit onto the substrate, wherein the third light-emitting unit and one of the first light-emitting unit and the second light-emitting unit are adjacent to each other in a row direction; and a projection of the second portion onto the substrate is within a projection of an area between respective two adjacent rows of the plurality of light-emitting units onto the substrate; and
   the second photosurface comprises a third portion; and a projection of the third portion onto the substrate is within the projection of the area between the first light-emitting unit and the second light-emitting unit onto the substrate, wherein the first light-emitting unit and the second light-emitting unit are adjacent to each other in the row direction.

4. The array substrate of claim 1, wherein a light brightness of the first light-emitting unit corresponding to the first fingerprint recognition unit is greater than a light brightness of another first light-emitting unit corresponding to the second fingerprint recognition unit.

5. The array substrate of claim 1, wherein a light brightness of the second light-emitting unit corresponding to the first fingerprint recognition unit is greater than a light brightness of another second light-emitting unit corresponding to the second fingerprint recognition unit.

6. The array substrate of claim 1, wherein each of the plurality of first fingerprint recognition units and each of the plurality of second fingerprint recognition units respectively comprise a photosensitive diode, a thin film transistor and a storage capacitor, wherein
an anode of the photosensitive diode is electrically connected to a first electrode of the storage capacitor and a cathode of the photosensitive diode is electrically connected to a second electrode of the storage capacitor and to a source electrode of the thin film transistor; a gate electrode of the thin film transistor is electrically connected to a switch control line; and a drain electrode of the thin film transistor is electrically connected to a signal line; and
the photosensitive diode is configured to convert a fingerprint signal light into a current signal.

7. The array substrate of claim 6, wherein
a capacitance value of the storage capacitor of each of the plurality of first fingerprint recognition units is less than that of each of the plurality of second fingerprint recognition units.

8. The array substrate of claim 7, wherein
a distance between the first electrode and the second electrode of the storage capacitor of each of the plurality of first fingerprint recognition units is greater than that of the storage capacitor of each of the plurality of second fingerprint recognition units; or
an enfilade area between the first electrode and the second electrode of the storage capacitor of each of the plurality of first fingerprint recognition units is less than that of the storage capacitor of each of the plurality of second fingerprint recognition units.

9. The array substrate of claim 1, wherein the plurality of first fingerprint recognition units and the plurality of second fingerprint recognition units are located as one of the following manners:
the plurality of first fingerprint recognition units and the plurality of second fingerprint recognition units are located between the substrate and the plurality of light-emitting units; or
the plurality of first fingerprint recognition units and the plurality of second fingerprint recognition units are located on a side of the substrate facing away from the plurality of light-emitting units; or
the plurality of first fingerprint recognition units and the plurality of second fingerprint recognition units are located on a side of the plurality of light-emitting units facing away from the substrate; or
the plurality of first fingerprint recognition units and the plurality of second fingerprint recognition units are located in a same layer as the plurality of light-emitting units, while each of the plurality of first fingerprint recognition units and the plurality of second fingerprint recognition units is between two adjacent ones of the plurality of light-emitting units.

10. A display panel, comprising an array substrate, wherein the array substrate comprises:
a substrate comprising a display area with a non-display area surrounding the display area;
a plurality of light-emitting units located in the display area of the substrate, wherein the plurality of light-emitting units comprise a plurality of first light-emitting units configured to emit first color light, a plurality of second light-emitting units configured to emit second color light, and a plurality of third light-emitting units configured to emit third color light, and wherein a light transmittance of the first color light and that of the second color light are both greater than that of the third color light; and
a plurality of first fingerprint recognition units and a plurality of second fingerprint recognition units, which are located in the display area of the substrate, wherein
a projection of each of the plurality of first fingerprint recognition units onto the substrate overlaps at least in part with a projection of an area between a respective one of the plurality of third light-emitting units and one of a respective one of the plurality of first light-emitting units, and a respective one of the plurality of second light-emitting units onto the substrate;
a projection of each of the plurality of second fingerprint recognition units onto the substrate does not overlap with the projection of the area between the third light-emitting unit and one of the first light-emitting unit and the second light-emitting unit onto the substrate; and
the projection of each of the plurality of second fingerprint recognition units onto the substrate overlaps at least in part with a projection of an area between the respective one of the plurality of first light-emitting units and the respective one of the plurality of second light-emitting units onto the substrate; wherein the plurality of light-emitting units are configured to: in a fingerprint recognition stage, serve as light sources for the plurality of first fingerprint recognition units and the plurality of second fingerprint recognition units, and the plurality of first fingerprint recognition units and the plurality of second fingerprint recognition units have different configuration parameters for detecting an electric signal value with respect to a reflector.

11. The display panel of claim 10, wherein the display panel is a liquid crystal display panel, and further comprises a color filter substrate opposite to the array substrate, and a liquid crystal layer between the array substrate and the color filter substrate.

12. The display panel of claim 10, wherein the display panel is an organic light-emitting display panel and further comprises a cover plate opposite to the array substrate.

13. A display device, comprising a display panel comprising an array substrate, wherein the array substrate comprises:
a substrate comprising a display area with a non-display area surrounding the display area;
a plurality of light-emitting units located in the display area of the substrate, wherein the plurality of light-emitting units comprise a plurality of first light-emitting units configured to emit first color light, a plurality of second light-emitting units configured to emit second color light, and a plurality of third light-emitting units configured to emit third color light, and wherein a light transmittance of the first color light and that of the second color light are both greater than that of the third color light; and a plurality of first fingerprint recognition units and a plurality of second fingerprint recognition units, which are located in the display area of the substrate, wherein a projection of each of the plurality of first fingerprint recognition units onto the substrate overlaps at least in part with a projection of an area between a respective one of the plurality of third light-emitting units and one of a respective one of the plurality of first light-emitting units, and a respective one of the plurality of second light-emitting units onto the substrate;

a projection of each of the plurality of second fingerprint recognition units onto the substrate does not overlap with the projection of the area between the third light-emitting unit and one of the first light-emitting unit and the second light-emitting unit onto the substrate; and the projection of each of the plurality of second fingerprint recognition units onto the substrate overlaps at least in part with a projection of an area between the respective one of the plurality of first light-emitting units and the respective one of the plurality of second light-emitting units onto the substrate; wherein the plurality of light-emitting units are configured to: in a fingerprint recognition stage, serve as light sources for the plurality of first fingerprint recognition units and the plurality of second fingerprint recognition units, and the plurality of first fingerprint recognition units and the plurality of second fingerprint recognition units have different configuration parameters for detecting an electric signal value with respect to a reflector.

* * * * *